United States Patent
Herndon

(10) Patent No.: US 7,848,799 B2
(45) Date of Patent: Dec. 7, 2010

(54) DRILL DEVICE AND METHOD FOR FORMING MICROCONDUITS

(75) Inventor: Terry O. Herndon, Carlisle, MA (US)

(73) Assignees: Path Scientific, LLC MA (US); Galderma Pharma S.A. (CH)

( * ) Notice: Subject to any disclaimer, the term of this patent is extended or adjusted under 35 U.S.C. 154(b) by 995 days.

(21) Appl. No.: 11/206,232

(22) Filed: Aug. 17, 2005

(65) Prior Publication Data
US 2006/0041241 A1    Feb. 23, 2006

Related U.S. Application Data

(63) Continuation of application No. PCT/US2004/008617, filed on Mar. 22, 2004.

(60) Provisional application No. 60/457,208, filed on Mar. 25, 2003.

(51) Int. Cl.
*A61B 5/05* (2006.01)

(52) U.S. Cl. .................................... 600/547

(58) Field of Classification Search ................ 600/547; 125/1; 29/407.05, 593, 1 R, 12, 15, 7; 408/146, 408/103, 108, 109, 136, 180; 175/20, 50, 175/55, 58, 87, 122, 170, 203, 316
See application file for complete search history.

(56) References Cited

U.S. PATENT DOCUMENTS

| | | | | |
|---|---|---|---|---|
| 3,552,239 A | * | 1/1971 | Yeaman et al. | ............ 408/146 |
| 3,785,230 A | | 1/1974 | Lokey | |
| 3,918,449 A | | 11/1975 | Pistor | |
| 4,205,445 A | | 6/1980 | Tzeng | |
| 4,391,358 A | | 7/1983 | Haeger | |
| 4,807,587 A | * | 2/1989 | Baetschmann et al. | ......... 125/1 |
| 5,058,688 A | * | 10/1991 | Scott et al. | ................. 175/20 |
| 5,115,567 A | | 5/1992 | Yang et al. | |
| 5,135,532 A | | 8/1992 | Baker | |
| 5,272,946 A | | 12/1993 | McCullough et al. | |
| 5,283,955 A | | 2/1994 | Liang | |
| 5,611,806 A | | 3/1997 | Jang | |
| 5,630,796 A | | 5/1997 | Bellhouse et al. | |
| 5,645,554 A | | 7/1997 | Hugh | |
| 5,759,159 A | | 6/1998 | Masreliez | |

(Continued)

OTHER PUBLICATIONS

Zipp, Impedance Controlled Skin Drilling, Med. & Biol. Eng. & Comput., 1983, 21, 382-384.*

(Continued)

*Primary Examiner*—Max Hindenburg
*Assistant Examiner*—Brian Szmal
(74) *Attorney, Agent, or Firm*—Banner & Witcoff, Ltd.

(57) ABSTRACT

The present invention relates to methods and devices for formation of microconduits in tissue, particularly using an impedance sensing drill to form microconduits. One embodiment of the invention is an impedance sensing drill comprising a drilling assembly, a control module, mechanically connected to the drilling assembly for controlling the depth of drilling by the drilling assembly; and a sensor, electrically connected to the drilling assembly and control module for detecting a change in an electrical impedance of a material being drilled. Another embodiment is a method of forming a microconduit in a material, which comprises the steps of drilling into the material, monitoring an electrical impedance of the material, and stopping the drilling into the material when a change in the impedance is detected, thereby forming microconduit.

15 Claims, 8 Drawing Sheets

U.S. PATENT DOCUMENTS

| | | |
|---|---|---|
| 5,843,114 A | 12/1998 | Jang |
| 6,136,008 A | 10/2000 | Becker et al. |
| 6,176,865 B1 | 1/2001 | Mauze et al. |
| 6,207,400 B1 | 3/2001 | Kwon |
| 6,301,500 B1 | 10/2001 | Van Herk et al. |
| 6,334,856 B1 | 1/2002 | Allen et al. |
| 6,391,005 B1 | 5/2002 | Lum et al. |
| 6,402,732 B1 | 6/2002 | Flower et al. |
| 6,569,143 B2 | 5/2003 | Alchas et al. |
| 6,572,580 B2 | 6/2003 | Feldman |
| 6,706,032 B2 | 3/2004 | Weaver et al. |
| 6,863,136 B2 * | 3/2005 | Bar-Cohen et al. ............ 175/55 |
| 7,205,738 B2 | 4/2007 | Chapman et al. |
| 2004/0204700 A1 | 10/2004 | Weaver et al. |
| 2004/0236269 A1 | 11/2004 | Marchitto et al. |
| 2006/0041241 A1 | 2/2006 | Herndon |
| 2006/0247795 A1 | 11/2006 | Gass et al. |

OTHER PUBLICATIONS

Pasquali, E. et al. "Measurement of the Electrical Skin Resistance During Skin Drilling" Psychophysiology Instrumentation, Mar. 1971; vol. 8, No. 2, pp. 236-238.

* cited by examiner

CUTAWAY VIEWS

10/11/02 Scised (600u) / drilled (160u) conduits

11/20/02 TH L.H. Pinky 1. hole from 11/18, r. hole from 11/19

DRILL DEVICE AND METHOD FOR FORMING MICROCONDUITS

PRIORITY CLAIM AND CROSS-REFERENCE TO RELATED APPLICATIONS

This application is a continuation of PCT Application No. PCT/US2004/008617 filed 22 Mar. 2004, which was published in English on 14 Oct. 2004 as WO 2004/086938 A2. The disclosure of this application is hereby incorporated herein by reference.

PRIORITY CLAIM

This application claims priority from commonly owned copending U.S. Provisional Patent Application No. 60/457,208 filed 25 Mar. 2003. The disclosure of this application is hereby incorporated herein by reference.

FIELD OF THE INVENTION

The present invention relates to a drill device and methods of using the same for the formation of small openings, channels, or holes in tissue (or other materials). These holes are called "microconduits" herein. These microconduits are preferably formed using an impedance sensing drill.

BACKGROUND OF THE INVENTION

Transdermal drug delivery, as the term is used generally, refers to permeation of the stratum corneum, the tough outer barrier of the skin, by a pharmaceutically active molecule. The stratum corneum, the thin (approximately 10-20 µm) outer layer of the epidermis, is dead tissue containing both multilamellar lipid barriers, and tough protein-based structures.

The epidermis, directly beneath the stratum corneum, also behaves as a lipid barrier. The dermis, directly beneath the epidermis, is permeable to many types of solutes. In the administration of a drug by topical application to skin, lipid-soluble drug molecules dissolve into and diffuse through the skin's multilamellar lipid bilayer membranes along a concentration gradient by virtue of the drug molecules solubility in the lipid bilayer; Transdermal drug delivery may be targeted to a tissue directly beneath the skin, or to capillaries for systemic distribution within the body by the circulation of blood.

The term transdermal drug delivery usually excludes hypodermic injection, long-term needle placement for infusion pumps, and other needles, which penetrate the skin's stratum corneum. Thus, transdermal drug delivery is generally regarded as minimally invasive. However, the low rate of transport of therapeutic molecules through the stratum corneum remains a common clinical problem.

It is an object of the present invention to provide a device and method that reduces or wholly overcomes some or all of the difficulties inherent in prior known devices and methods. Particular objects and advantages of the invention will be apparent to those skilled in the art, that is, those who are knowledgeable or experienced in this field of technology, in view of the following disclosure of the invention and detailed description of certain preferred embodiments.

SUMMARY OF THE INVENTION

The present invention relates to methods and devices for formation of microconduits in tissue, particularly using an impedance sensing drill to form microconduits.

One embodiment of the invention is an impedance sensing drill comprising a drilling assembly, a control module, mechanically connected to the drilling assembly for controlling the depth of drilling by drilling assembly; and a sensor, electrically connected to the drilling assembly and control module for detecting a change in an electrical impedance of a material being drilled.

Another embodiment is a method of forming a microconduit in a material, which comprises the steps of drilling into the material, monitoring an electrical impedance of the material, and stopping the drilling into the material when a change in the electrical impedance is detected, thereby forming a microconduit.

Yet another embodiment is a method for drug delivery which comprises the steps of drilling into a target area, monitoring an electrical impedance of the target area, stopping the drilling into the target area when a change in the electrical impedance is detected, thereby forming a microconduit, and administering drug via the formed microconduit.

Another embodiment is a method of removing an analyte, which comprises the steps of drilling into a target area, monitoring an electrical impedance of the target area, stopping the drilling into the target area when a change in the electrical impedance is detected, thereby forming a microconduit, and removing the analyte via the formed microconduit.

Thus, in accordance with a first aspect, disclosed herein is an impedance sensing drill having a drilling assembly, a control module, mechanically connected to the drilling assembly for controlling the depth of drilling by drilling assembly; and a sensor, electrically connected to the drilling assembly and control module for detecting a change in an electrical impedance of a material being drilled.

Thus, in accordance with a second aspect, disclosed herein is a method of forming a microconduit in a material involving: drilling into the material, monitoring an electrical impedance of the material, and stopping the drilling into the material when a change in the electrical impedance is detected, thereby forming a microconduit.

Thus, in accordance with another aspect, disclosed herein is a method for drug delivery involves drilling into a target area, monitoring an electrical impedance of the target area, stopping the drilling into the target area when a change in the electrical impedance is detected, thereby forming a microconduit, and administering drug via the formed microconduit.

Thus, in accordance with another aspect, disclosed herein is a method of removing an analyte involves drilling into a target area, monitoring an electrical impedance of the target area, stopping the drilling into the target area when a change in the electrical impedance is detected, thereby forming a microconduit, and removing the analyte via the formed microconduit.

As described above, one aspect of the invention is an impedance sensing drill comprising a drilling assembly, a control module mechanically connected to the drilling assembly for controlling the depth of drilling by drilling assembly; and a sensor, electrically connected to the drilling assembly and control module for detecting a change in an electrical impedance of a material being drilled.

As described above, one aspect of the invention is a method of forming a microconduit in a material, which comprises the steps of drilling into the material, monitoring an electrical impedance of the material, and stopping the drilling into the material when a change in the electrical impedance is detected, thereby forming a microconduit.

As described above, one aspect of the invention is a method for drug delivery which comprises the steps of drilling into a target area, monitoring an electrical impedance of the target area, stopping the drilling into the target area when a change in the electrical impedance is detected, thereby forming a microconduit, and administering drug via the formed microconduit.

As described above, one aspect of the invention is a method of removing an analyte, which comprises the steps of drilling into a target area, monitoring an electrical impedance of the target area, stopping the drilling into the target area when a change in the electrical impedance is detected, thereby forming a microconduit, and removing the analyte via the formed microconduit.

As described above, one aspect of the invention is a method of painlessly producing microconduits in nails to treat onychomycosis and other infections of the nail and nail bed, which comprises the steps of drilling into a target area, monitoring an electrical impedance of the target area, stopping the drilling into the target area when a change in the electrical impedance is detected, thereby forming a microconduit, and treating the nail or nail bed infection with medication.

As described above, one aspect of the invention is a method of painlessly removing the stratum corneum layer of the skin to permit rapid infusion of drugs into the body, which comprises the steps of drilling into a target area, monitoring an electrical impedance of the target area, stopping the drilling into the target area when a change in the electrical impedance is detected, thereby forming at least one microconduit, and infusing drugs into the body through the microconduit.

As described above, one aspect of the invention is a method of entry into the brain cavity when drilling through the skull, which comprises the steps of drilling into a target area, monitoring an electrical impedance of the target area, stopping the drilling into the target area when a change in the electrical impedance is detected, thereby forming a microconduit in the skull having the appropriate depth in the brain cavity.

As described above, one aspect of the invention is a method of painlessly producing a microconduit in a nail to treat subungual hematomas, which comprises the steps of repeatedly drilling into a target area, monitoring an electrical impedance of the target area, stopping the drilling into the target area when a change in the electrical impedance is detected, thereby forming a plurality of microconduits, and infusing drugs into the nail through the microconduit.

As described above, one aspect of the invention is a method of painlessly removing the stratum corneum from the epidermis to permit iontophoretic infusion of drugs into the body over a lengthy time period, which comprises the steps of drilling into a target area, monitoring an electrical impedance of the target area, stopping the drilling into the target area when a change in the electrical impedance is detected, thereby forming a microconduit, and placing a drug containing patch over the microconduit to permit iontophoretic infusion of drugs into the body.

As described above, one aspect of the invention is a method of painlessly removing the stratum corneum from the epidermis to permit electroporation of the skin to deliver drugs into the body over a lengthy time period, which comprises the steps of drilling into a target area, monitoring an electrical impedance of the target area, stopping the drilling into the target area when a change in the electrical impedance is detected, thereby forming a microconduit, and treating the microconduit containing area with means to permit electroporation of the skin to deliver drugs into the body.

As described above, one aspect of the invention is a method to limit the penetration of the skin by any electrically controlled apparatus capable of penetrating the skin by detecting such penetration by monitoring the electrical impedance between the apparatus and an ECG electrode attached to the person and if the in vivo impedance falls below a predetermined resistance, sending an electrical signal that reverses the direction of the penetrating apparatus, or stops the motion of the penetrating apparatus, which comprises the steps of drilling into a target area, monitoring an electrical impedance of the target area, stopping the drilling into the target area when a change in the electrical impedance is detected, thereby forming a microconduit, and controlling the penetration of the apparatus.

As described above, one aspect of the invention is a method of painlessly removing the stratum corneum from the epidermis in one or more locations to permit the reduction of the electrical impedance between two or more ECG or other electrodes attached to the skin over the sites having the stratum corneum removed, which comprises the steps of drilling into a target area, monitoring an electrical impedance of the target area, stopping the drilling into the target area when a change in the electrical impedance is detected, thereby forming a microconduit, and controlling the removal of the stratum corneum based upon a predetermined change in the electrical impedance.

As described above, one aspect of the invention is a method of painlessly removing the stratum corneum from the epidermis to permit pressurized delivery of drugs into the body, which comprises the steps of drilling into a target area, monitoring an electrical impedance of the target area, stopping the drilling into the target area when a change in the electrical impedance is detected, thereby forming a microconduit, and providing means for the pressurized delivery of drugs into the body through the microconduit.

As described above, one aspect of the invention is a method of painlessly removing the stratum corneum from the epidermis to permit rapid infusion of an anesthetic agent into the body under no pressure, which comprises the steps of drilling into a target area, monitoring an electrical impedance of the target area, stopping the drilling into the target area when a change in the electrical impedance is detected, thereby forming a microconduit, and topically administering an anesthetic to the site of the microconduit. Preferably, the anesthetic is Lidocaine.

As described above, one aspect of the invention is a method of painlessly removing the stratum corneum from the epidermis to permit extraction of analyte from the body, which comprises the steps of drilling into a target area, monitoring an electrical impedance of the target area, stopping the drilling into the target area when a change in the electrical impedance is detected, thereby forming a microconduit, and extracting analyte from the body through the microconduit. Preferably, the analyte is a blood sample. Alternatively, the analyte may be a tissue sample or an interstitial fluid sample.

As described above, one aspect of the invention is a method of painlessly removing the stratum corneum from the epidermis to permit blood collection from the body for analysis, which comprises the steps of drilling into a target area, monitoring an electrical impedance of the target area, stopping the drilling into the target area when a change in the electrical impedance is detected, thereby forming a microconduit, and removing blood from the body through the microconduit.

As described above, one aspect of the invention is a method of marking nail tissue with at least one identifying mark which comprises the steps of drilling into the target area with a drill, monitoring an electrical impedance of the target area, and stopping the drilling into the target area when a change in the electrical impedance is detected, thereby forming a mark on the nail tissue. Optionally, a dye may be placed in the formed mark to add coloration.

As described above, one aspect of the invention is a method of tattooing skin tissue which comprises the steps of drilling into the target area, monitoring an electrical impedance of the target area, stopping the drilling into the target area when a change in the electrical impedance is detected, thereby forming a microconduit, and inserting dye into the formed microconduit.

In accordance with another aspect, an impedance sensing drill comprises a drilling assembly, a control module mechanically connected to the drilling assembly for controlling the depth of drilling by the drilling assembly; a sensor, electrically connected to the drilling assembly and control module for detecting a change in an electrical impedance of a material being drilled; and a mount allowing the impedance sensing drill to move in at least one direction parallel to a surface being drilled. The mount may also allow movement in a direction perpendicular to the surface being drilled. Preferably, when in this configuration, the impedance sensing drill is computer controlled.

As described above, one aspect of the invention is a method of painlessly removing the stratum corneum from the epidermis to permit long term diffusion of drugs into the body, which comprises the steps of drilling into a target area, monitoring an electrical impedance of the target area, stopping the drilling into the target area when a change in the electrical impedance is detected, thereby forming a microconduit, and placing a drug containing patch over the microconduit to permit long term diffusion of drugs into the body.

As described above, one aspect of the invention is a method of painlessly removing the stratum corneum from the epidermis in one or more locations to permit the reduction of the electrical impedance between an ECG or other electrode and the interior of the body for improved monitoring of body electrical signals, which comprises the steps of drilling into a target area, monitoring an electrical impedance of the target area, stopping the drilling into the target area when a change in the impedance is detected, thereby forming a microconduit, controlling the removal of the stratum corneum based upon a predetermined change in impedance, and attaching an ECG or other electrode to the skin over the site having the stratum corneum removed.

As used herein the terms impedance and electrical impedance are used interchangeably. In some embodiments the impedance characteristic focused on is resistance. Those skilled in the art would understand the relationship between resistance and impedance and recognize that in certain applications or embodiments monitoring the resistance is one method of monitoring the impedance.

These and additional features and advantages of the invention disclosed herein will be further understood from the following detailed disclosure of certain preferred embodiments.

Figure 1:
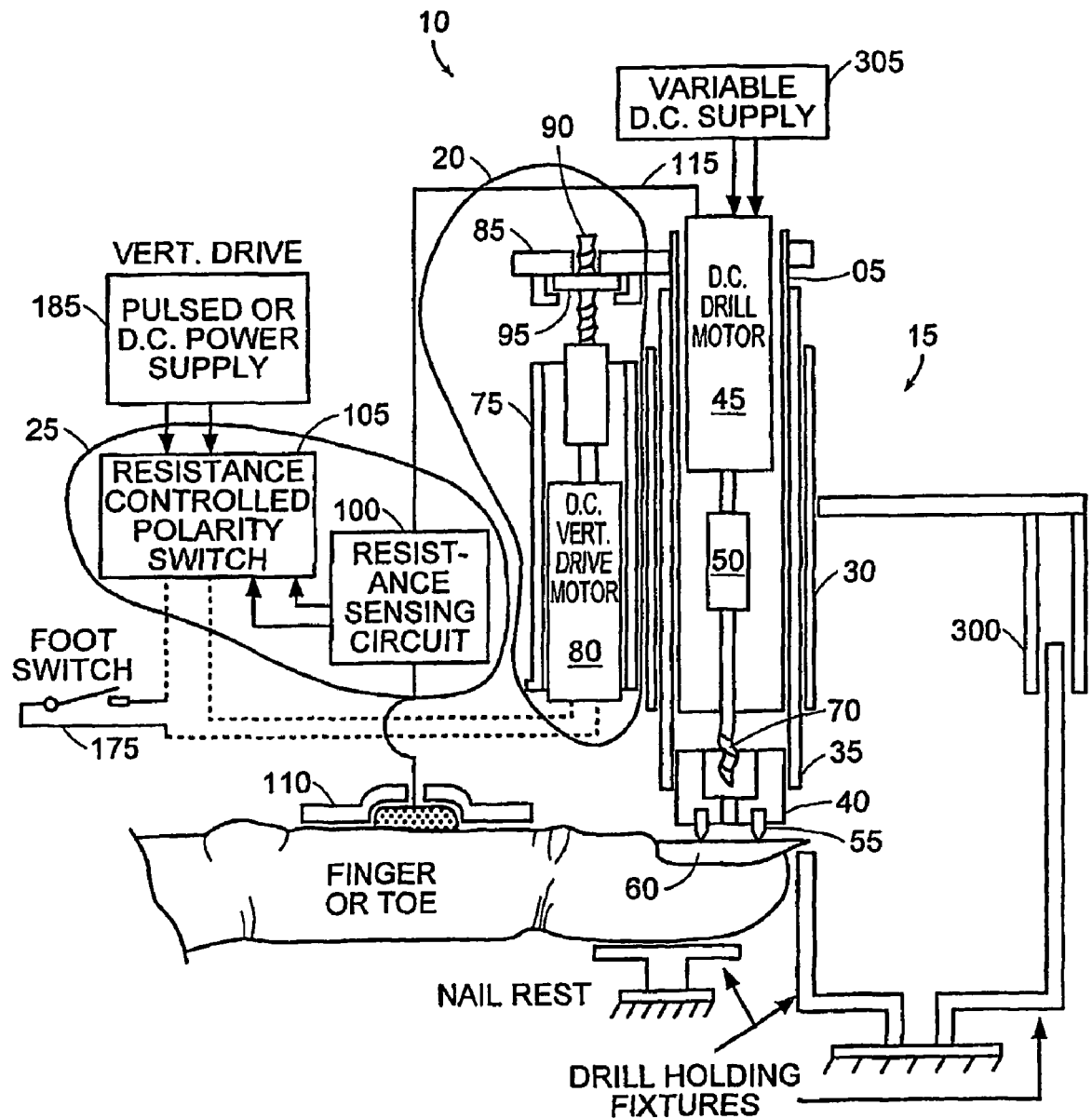
FIG. 1 is a schematic of a preferred embodiment of the invention showing an impedance sensing drill 10 comprises a drilling assembly 15, a control module 20, mechanically connected to the drilling assembly 15 for controlling the depth of drilling by the impedance sensing drill 10; and a sensor 25, electrically connected to the drilling assembly 15 and control module 20 for detecting a change in the electrical impedance of a material being drilled.

The figures referred to above are not drawn necessarily to scale and should be understood to present a representation of the invention, illustrative of the principles involved. Some features of the invention depicted in the drawings have been enlarged or distorted relative to others to facilitate explanation and understanding. Inventions as disclosed herein, will have configurations and components determined, in part, by the intended application and environment in which they are used.

DETAILED DESCRIPTION OF CERTAIN PREFERRED EMBODIMENTS

As used herein, the term microconduit refers to a small opening, channel, or hole into or through, a material, that allows transfer of materials by liquid flow, diffusion, convection or electrophoresis. The average size of microconduits according to an embodiment is about one (1) mm or less in diameter. In an embodiment, a microconduit has a diameter in the range of between about one 10 micrometers and about 200 micrometers (micron or μm). In another embodiment, the microconduit has a diameter in the range about 2 micrometers and about one (1) mm. In an embodiment, a microconduit is usually smaller than needles used for syringe injections, but has a characteristic size or diameter that is much larger than the diameter of carriers of analyte molecules, therapeutic molecules and ions, or the diameters of analyte molecules, therapeutic molecules and ions themselves. As used herein, the term diameter refers to the approximate diameter or characteristic linear dimension of at least one cross-section of an approximately cylindrical-shaped section of a micro conduit.

Many materials, including organic materials exhibit properties such as electrical impedance, expressed in Ohms. Different materials very often possess different electrical impedances. Therefore transition between levels or layers of different materials can be determined by a change in measured electrical impedance. Therefore by measuring impedance during formation of a microconduit, if the impedance change is great enough, precise control of depth of the microconduit can be maintained. Using such a method, the microconduit is formed only in certain layers, allowing access to lower layers without damage to the lower layers.

The forming of such microconduits is particularly useful in organic material where only certain layers or materials need to be penetrated. Examples of organic materials that microconduits can be formed in, include but are not limited to: tissue, including the stratum corneum, epidermis, and dermis, cartilage, nails, and bone. Controlling the depth of the microconduit allows for access to the desired layer, material or tissue while minimizing the trauma to the layer, material, or tissue for which access is not desired.

In a preferred embodiment, as shown in FIG. 1, an impedance sensing drill 10 comprises a drilling assembly 15, a control module 20, mechanically connected to the drilling assembly 15 for controlling the depth of drilling by the impedance sensing drill 10; and a sensor 25, electrically connected to the drilling assembly 15 and control module 20 for detecting a change in an impedance of a material being drilled.

In a preferred embodiment the drilling assembly 15 comprises a first housing 30, a second housing 35 configured for mounting in the first housing 30, a third housing 05 slideably configured within the second housing 35, an electrically insulated nosepiece 40 attached to the second housing 35, a drill motor 45 electrically isolated from the third housing 05 and mounted within the third housing 05, and a drill collar 50 for receiving bits 70 used in drilling.

The first 30 and second 35 and third 05 housings are preferably made of metal and sized so that the third housing is slidable within the second housing while containing the drill motor 45. The drill motor 45 is preferably a dc motor with suitable power to form microconduits in the material being drilled, suitable d.c. motors include, but are not limited to, a micromotor by RMB Miniature Bearing of Ringwood N.J., and MOT 1009 or MOT 1025 by B.G. Micro of Garland Tex.

Figure 2:
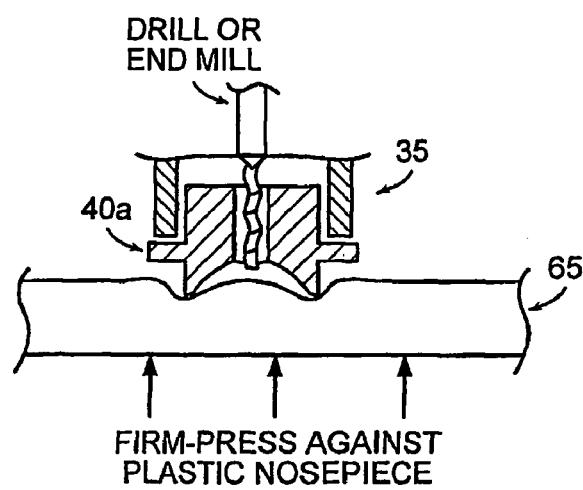
FIG. 2 shows a preferred electrically insulating nosepiece arrangement 40a for use with the impedance sensing drill of FIG. 1.

The nosepiece 40 is typically made of a non-conducting material so as to minimize the risk of electrical shock to tissue or organic matter the drill assembly is being used on. Also the nonconductive nosepiece eliminates any possible electrical impedance parallel paths between the drill/endmill "sending electrode" and the resistance sensing circuit 100. The nosepiece 40 shown in FIG. 1, is made of plastic and typically contains three or four feet 55. These acts to rigidly locate the entire drill assembly 15 to the outer surface of the material being drilled (here a nail 60). In other embodiments the nosepiece 40 may be adapted for use on other materials or surfaces. An example of such can be seen in FIG. 2 wherein the nosepiece 40a is made of Teflon and adapted for use on skin 65.

The nosepiece 40 shown in FIG. 1 is attached to the second housing 35. The second housing 35 is clamped by the first housing 30 in an adjustable manner. When unclamped, the nosepiece 40 can be positioned vertically with reference to the drill bit 70 and clamped. The first housing 30 is attached to the holding arm 300 that holds the entire mechanical assembly over the target area.

Referring again to FIG. 1, the collar 50, also referred to as a chuck, is preferably of a size and material suitable for attaching a bit 70 the drill motor 45. In a preferred embodiment the collar 50 is made out of an electrically conductive material allowing for electrical impedance sensing through the drill motor 45 to the drill bit 70 in contact with the material being drilled. Examples of suitable collar materials include, but are not limited to, stainless steel, brass and steel.

In preferred embodiments the control module 20 comprises a housing 75, a vertical drive motor 80, and a support arm 85. The housing 75 is preferably made of metal and attached to the first housing 30 of the drilling assembly 15. The vertical drive motor 80 is mounted in the housing 75. In preferred embodiments the vertical drive motor 80 is a d.c. motor. Suitable vertical drive motors include, but are not limited to micromotor by RMB Miniature Bearing of Ringwood N.J., and MOT 1009 or MOT 1025 by B.G. Micro of Garland IX.

The support arm 85 is connected to the third housing 05 of the drilling assembly and mounted on a screw track 90 attached the vertical drive motor 80. In this configuration, as the vertical drive motor 80 rotates the support arm 85 travels along the screw 90 thereby raising or lowering the third housing 05 of the drilling assembly as well as the drill motor 45 and attached drill bit 70. The embodiment shown in FIG. 1 uses a captive nut 95 on the support arm 85 to effect the vertical movement along the screw track 90.

In a preferred embodiment the sensor 25 is electrically connected to the drill motor 45 of the drilling assembly 15 as well as the control module 20 for detecting a change in an impedance value of a material being drilled. In preferred embodiment the sensor 25 comprises a resistance sensing circuit 100, and a polarity switch 105. As shown in FIG. 1, the resistance sensing circuit 100 has a first electrode 110 placed in contact with the material of which electrical impedance is being measured. A second connection 115 is made from the resistance sensing circuit 100 to the drill motor 45 such that the drill bit 70, in electrical connection with the motor 45 though the collar 50, acts like a second electrode in contact with the material in which an electrical impedance change is being measured. The polarity switch 105 of the sensor 25 is electrically connected to the vertical drive motor 80 of the control module 20. When a change is detected in the impedance being measured a signal is sent to the control module 20 reversing the direction of the vertical drive motor 80.

In a preferred embodiment of the sensor 25, the electrical impedance characteristic being measured is electrical resistance. An example of a sensor 25 for measuring resistance can be seen in FIG. 3. A 500 c.p.s. supply 130 consists of an ICM7555 timer 135 that switches on-off at 500 cycles per second. This drives relay W171DIP-7140 that switches the 1.1 v output from the 1.5V battery 145 on and off to the first electrode 110 on the material being drilled (here a nail 60). This causes current to flow thru the material on thru the drill bit 70 and drill motor 45 to the resistance sensing circuit 100. The current is measured by the operational amplifier OP27EZ 150, amplified and sent to the LM 311 voltage comparator 155. When the op-amp output reaches the value representing the desired input resistance (here 15K-35 K ohms), which is adjusted by Rset 160, the volt comparator 155 output goes to ground. This causes the contacts in the two W171DIP25s 165, 170 to close. If the switch 175 (here a foot pedal) has been held closed, moving the drill down, a first relay 165 closes, putting +15V on the polarity reversing switch coil 180 that hooks the vertical drive D.C. supply 185 to the vertical drive motor 80 in such a way as to pull the drill out (away) from the hole it has been drilling. A second latch push button 190 is normally closed. The second relay 170 was closed by the change in the measured resistance along with the first relay 165. The second relay 170 forces the relays 165, 170 to stay closed even when the drill comes out and the measured resistance returns high, to 5 meg ohms. This is done because otherwise, as soon as the drill left the drilled area and the measured resistance returned to 5 meg ohms, the circuit would reverse the vertical drive motor downward again. When the switch 175 is turned off, the second latch push button 190 can be pressed causing the relays 165, 170 to open and the drill to function normally again.

A first push button 195 serves to permit manual operation. After the second push button 190 is actuated, the system is ready for down (high resistance) operation. Pushing the switch 175 will move the drill down. Opening the switch 175 will stop the vertical drive motor 80. In certain embodiments the vertical drive motor 80 may be left energized but stalled to produce a steady downforce. Pressing the normally open first push button 195 puts the 11 K ohm (low resistance) from the 500 c.p.s. power supply 130 to the sense circuit that latches the latch and reverses the vertical drive motor 80, lifting the drill. The 500 c.p.s. 1.1V power supply 130 is completely self-contained with its 1.5V battery 200 electrical source eliminating the possibility of the material being drilled being exposed to alternating current from the wall socket and possibly being injured.

In the polarity switch 105, the large 2200 micro farad capacitor 205 and diode 210 put a full voltage, approximately one second wide pulse, on the vertical drive motor 80 to very quickly lift the drill from the hole in the material being drilled. When drilling into the material, the diode 210 blocks full voltage from the vertical drive motor 80 and the 40 ohm resistor 215 across the diode 210 reduces the voltage to approximately 3V rather than the 12V of the withdrawing pulse.

Referring again to FIG. 1, in a preferred embodiment the impedance sensing drill is typically mounted on a stand 300 in the proximity of the material being drilled. The drilling assembly 15, control module 20, and sensor 25 are connected to first 305 and second 185 power supplies. The first power supply 305 is a variable d.c. power supply for supplying electrical power to the drill motor. The second power supply 185 is either a variable or pulsed d.c. power supply for powering the vertical drive motor. Suitable power supplies include, but are not limited to a LP521FM by Lambada Co., Melville, N.Y., and a 721A, by Hewlett Packard Co., San Diego, Calif. The first electrode 110 is placed in contact with the material in which a microconduit is to be formed. The drilling of the microconduit is controlled by a switch 175, such as a foot pedal. An example of a suitable switch for controlling the drilling is a T-51-S, by Linemaster Switch Co., Woodstock, Conn. The user initiates drilling, by activating the control switch 175 (here a foot petal). When a change in the measured electrical impedance between first electrode 110 and the second electrode 70 (drill bit) is detected by the sensor 25, the sensor 25 sends a signal reversing the vertical direction of the drill, effectively stopping the drilling by removing the drill bit from the material.

Figure 4:
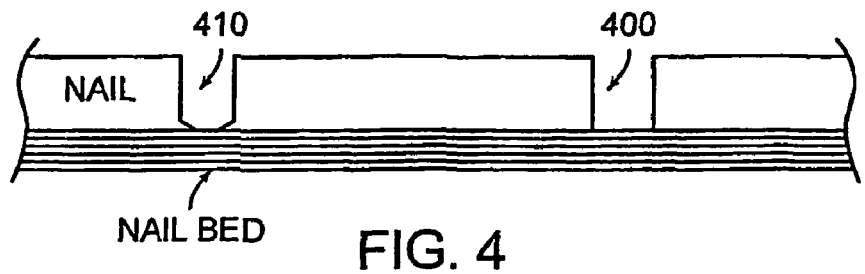
FIG. 4 illustrates an endmill generated microconduit with a flat or squared-off bottom 400 as opposed to the tapered bottom 410 formed by a traditional drill bit.

In another preferred embodiment, an endmill is used in the formation of a microconduit. The endmill is connected to the drill motor of the drilling assembly via the collar 50. Suitable endmill bits include, but are not limited to, carbide endmills such as those made by Performance Micro Tool, Janesville, Wis. In certain preferred embodiments the endmill is 0.010 inches in diameter. In certain applications is may be beneficial to produce a microconduit with a flat or squared-off bottom as opposed to the tapered bottom formed by a traditional drill bit as shown in FIG. 4. Here a microconduit formed by an endmill 400 allows for greater access to the nail bed through a nail than a microconduit formed using a tradition drill bit 410.

Figure 5:
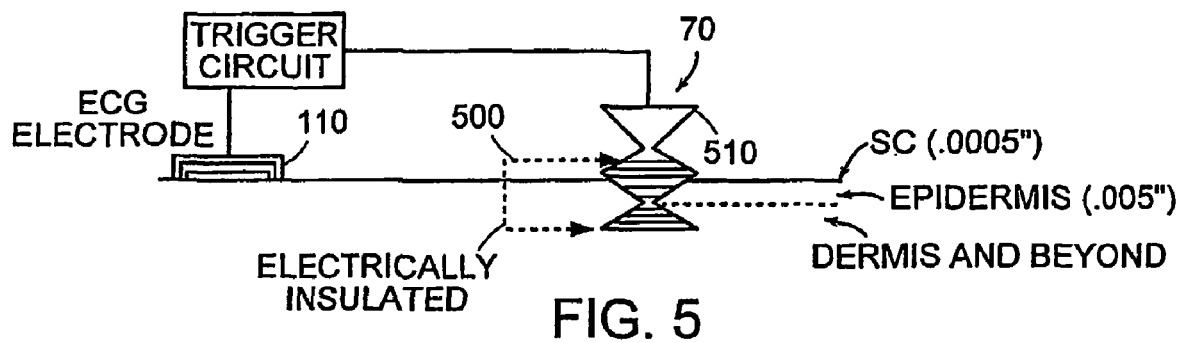
FIG. 5 shows a depth control feature in which having a predetermined portion of the drill bit covered in a non-conducting material may precisely set the depth of a microconduit.

In another embodiment the tip of the drill/mill is partially covered in a non-conducting material. The depth of a microconduit may also be precisely set by having a predetermined potion of the drill bit covered in a non-conducting material. In this embodiment, as seen in FIG. 5, when the drill bit 70 has penetrated the material past the portion of drill bit covered in the non-conducting material 500, a change in the measured electrical impedance is detected, here indicated as a circuit being formed by the uncoated portion 510 and the first electrode 110, and the drilling is stopped and the drill bit removed leaving a microconduit of predetermined depth.

Figure 6A:
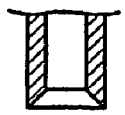
FIG. 6 shows an example of a bit with a sharpened hollow tip or with sharpened serrated edges, which would allow for extraction or implantation of material.
Figure 6B:
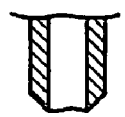
Figure 6C:

In another embodiment the bit may be hollow with a serrated edge as shown in FIG. 6. Being hollow would allow for extraction or implantation of material. Possible applications include biopsies or hair implantation.

In a preferred embodiment a method of forming a microconduit comprises, drilling into a material in which a microconduit is to be formed, monitoring an electrical impedance of the material; and stopping the drilling into the material when a change in the electrical impedance being monitored is detected.

In another preferred embodiment, a method of forming an opening in the stratum corneum of skin comprises drilling into skin where a microconduit is to be formed, monitoring an electrical impedance of the skin; and stopping the drilling into the skin when a change in the electrical impedance being monitored is detected. In one embodiment the stratum corneum is removed from the epidermis in one or more locations to permit the reduction of the electrical impedance between two or more ECG or other electrodes attached to the skin over the sites having the stratum corneum removed. In other embodiments microconduits can be formed though other layers of skin. Additional embodiments may have microconduits passing entirely though the skin or other such tissue.

In another preferred embodiment, a method of delivering drugs comprises, drilling into the target area to receive drug, monitoring an electrical impedance of the target area, stopping the drilling into the target area when a change in the electrical impedance being monitored is detected thereby forming a microconduit, and administering the drug though the microconduit.

In accordance with another embodiment, the above techniques may be used to remove the stratum corneum to permit electroporation of the skin to deliver drugs into the body over a lengthy time period. In other embodiments the stratum corneum is removed to allow rapid infusion of drugs into the body under no pressure In another preferred embodiment, a method of extracting an analyte comprises drilling into the target area where analyte is to be extracted, monitoring an electrical impedance of the target area, stopping the drilling into the target area when a change in the electrical impedance being monitored is detected thereby forming a microconduit, and removing the analyte though the microconduit. In certain preferred embodiments, the analyte being extracted is a blood sample as discussed in more detail in the experiments described in the specification below. Other applications may include biopsies, fluid drainage, or the like. Other embodiments and applications will be apparent to one skilled in the art given the benefit of this disclosure.

In another preferred embodiment, a method for forming at least one microconduit through a nail comprises drilling into the nail, monitoring an electrical impedance of the region of the drilling, and stopping the drilling into the nail when a change in the electrical impedance being monitored is detected, thereby forming a microconduit. By forming a microconduit in a nail, drugs may be administered to tissue otherwise protected by the nail.

In certain preferred embodiments this technique may be used to painlessly produce microconduits in nails to treat Onychomycosis and other infections of the nail and nail bed. In another embodiment this technique may be used to painlessly produce a microconduit in a nail to treat subungual hematomas.

This technique may also be effective for drilling through bone or other hard protective biological materials such as cartilage.

What follows here below are experiments performed using the apparatus and techniques described. These experiments are but a few of the possible applications and should not be viewed as a compressive list or discussion.

Experiment 1

Controlled Microconduit Drilling through Nails

Figure 7:
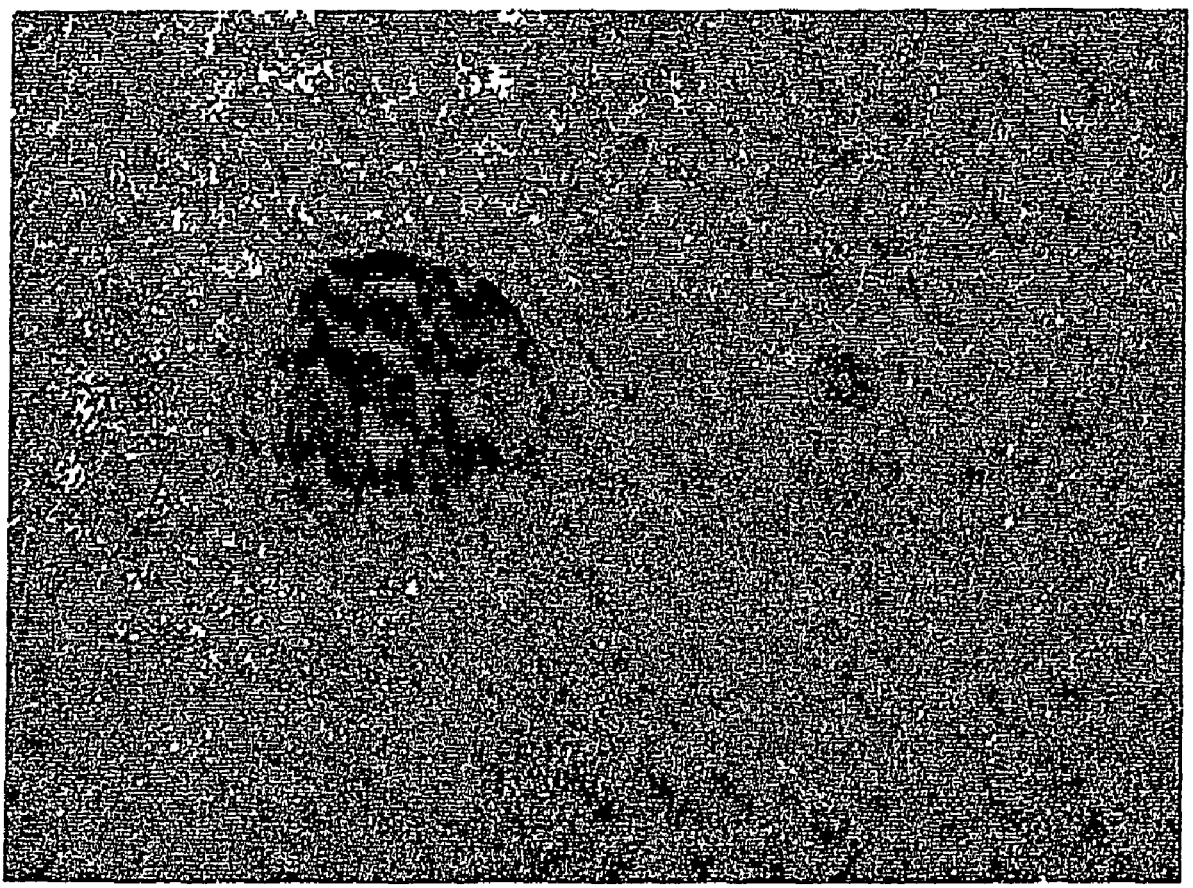
FIG. 7 is a photograph of a normally scised micro conduit that is 550-600 μm in diameter next to a 160 μm diameter micro conduit that was drilled in the overhang of a left ring finger nail using a 0.006 inches in diameter (150 μM) twist drill.

A number of experiments have been done with mechanically drilling holes through the nail. FIG. 7 shows a normally scised micro conduit that is 550-600 μm in diameter next to a 160 μm diameter micro conduit that was drilled in the overhang of a left ring finger using a 0.006 inches in diameter (150 μm) twist drill in a precision drill press.

This approach has the advantages of making smaller size openings and permitting mechanical measurement of the drill depth below the surface of the nail via dial indicator monitoring. Also, depth determination into the nail bed can be determined through electrical resistance (impedance) measurements. An electrical contact to the quill of the drill press was established by using a ball bearing on a flex spring to permit real time resistance measurement with the rotating quill/chuck/drill. Thus, using an ECG electrode on the skin of the wrist as reported earlier, one can measure the electrical resistance between the drill and the electrode while drilling (SR 720 LCR meter, lv., lkc). The resistance stayed in the 3-5 Meg ohm range for most of the distance, then at 0.016 inches (400 μM) drill depth from the nail surface (dial indicator measurement), the electrical resistance began dropping through 1 meg ohm, 500 K ohms, 100 K ohms over the next 50 μm drill depth. As the drill has a vernier vertical quill positioning knob, it was easy to determine that the 100 K ohm-25 K ohm decline occurred over a 25 μm range. Then a slight bit further, a 15 K ohm resistance was reached and drilling stopped. There was no sensation at all, and no blood. However, close microscopic examination revealed that blood was to be seen deep in the microconduit.

Electric motors 0.120 inch (3 mm) in diameter by 0.325 inch (8 mm) long are available. This is small enough to permit location in a fixture standing on the nail. Also, junk stores have cell phone vibrator motors that are 0.250 inch (6 mm) diameter by 0.65 inch (16 mm) long. The chuck is made by drilling a 0.125 inch diameter brass rod with a hole to press fit the shaft of the vibrator motor, and a hole on the other end with a 0.013 inch drill. Breaking off the blank end of the 0.013 inch drill bends it enough and leaves a tiny, sharp tang on its end so that when pressed in to the 0.013 inch hole, it is firmly enough held to permit drilling aluminum or fingernail.

The above arrangement was mounted in a ⅜ inch diameter, 1.25 inch long brass rod, machined to ⅛ inch for a quarter inch, and drilled out on the big end to accept the ¼ inch diameter motor. This permits mounting the minimotor in the sensitive drill to provide downforce and mechanical down distance measurement for testing drilling efficacy, drill containment and ability to measure resistance through the minimotors bearings/chuck/drill.

Test drilling in a left hand ring finger overhang showed that there was no slippage between the drill and the chuck. The motor/chuck/drill feed was done manually through the vernier feed knob built into the sensitive drill. Also, depth can be visually monitored to ½ mil (10 pun) through a dial indicator built into the system. The drill would not self-center, simply wobbling without center punching a dimple into the nail. The motor nominally runs on 1.5-2 volts, but at the 1.5 volt level it would stall while drilling through the 0.016 inch thick nail. Increasing the voltage to 2.5V provided enough power to prevent stalling with a slow (ca 2-3 mils per sec.) feed. The drill is estimated to have been turning at 600-1500 rpm.

Drilling a hole through the nail to the nail bed while making real-time resistance measurements using a SRS 715 LCR meter using 1 volt, 1 KHz settings was then tested. As the drilling progressed the resistance remained in the 2-5 meg ohm range. As drilling neared the nail bed a hot sensation could be felt over a fairly large area. The resistance remained in the 2-5 Meg ohm range, indicating no drilling into the nail bed. Also, drill chips were still coming out of the hole. It turned out that the sensation was due to heat produced by the drilling process. Slowing down the feed rate reduced the heating to the extent that it couldn't be felt. As the drill entered the nail/bed region, the resistance began dropping through 1 Meg ohm to 500 K ohms to 100 K ohms on down to 10 K ohms and perhaps to 6 K ohms, the digital readout was jumping around in this range. There was no sensation of any sort into these resistance ranges. Microscopic inspection of the conduit showed very slight, non-flowing blood at its bottom. It was decided to use a larger drill here since the 160 μm hole seemed too small to allow drug delivery, such as a fungicide cream.

Figure 9:
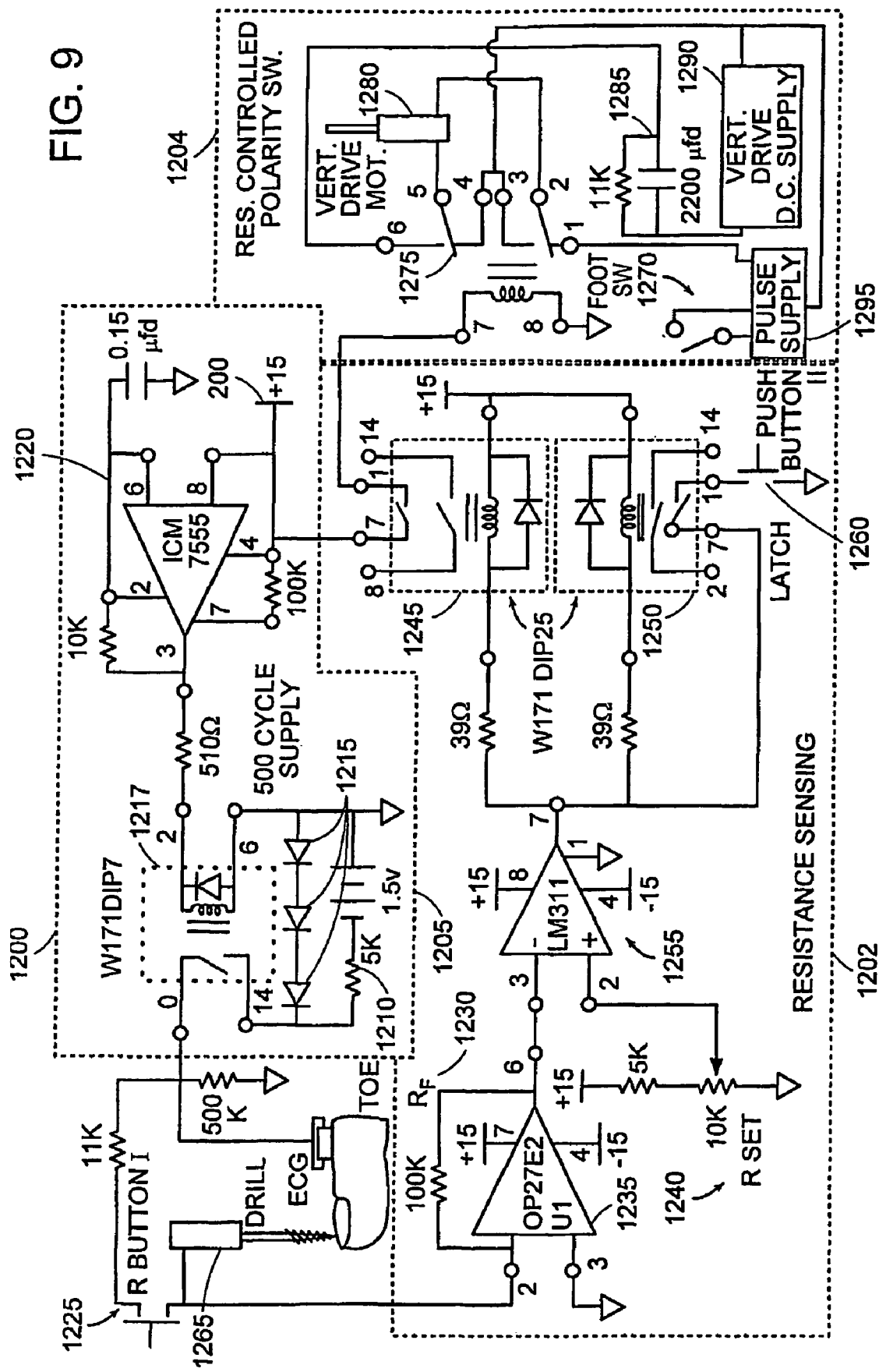
FIG. 9 is a circuit diagram for the FIG. 8 small drill arrangement to permit controlled drilling of a nail by referencing to its top surface.

FIG. 9 is an illustration of an embodiment of a small drill arrangement to permit controlled drilling of a nail by referencing to its top surface. The size of this system is 0.5 inch× 1.25 inch×1.25 inch. It consists of a drilling assembly 850, a control module 860 and a sensor 870. The control module 860 includes a vertical drive motor 900 connected to a 1-72 screw 910 by means of a collar 915. The control module also has an arm 950 carrying a captive 1-72 nut 955 mounted on the screw 910. The motor 900 is pressed into a housing 920 that is soldered to a first housing 925 of the drilling assembly 850.

The drilling assembly 850 includes a drill motor 905 connected to a drill 930 by a close-fitting collar 935. The end of the drill motor shaft 940 is slotted, while the end of the drill 930 is ground flat, like a screwdriver. The end of the collar 935 into which the drill is inserted has double-sided sticky tape on it, through which the drill 930 is pushed. Thus, the drill 930 is twisted by the slotted drill motor shaft 940, and the drill 930 is held in the collar 935 by the sticky tape. The drill motor 905 is pressed into and electrically insulated from a third housing 945 of the drilling assembly 850, the outer end of which is connected to the arm 950 carrying the captive 1-72 nut 955 mounted on the screw 910 of the control module 860. The third housing 945 slides into a second housing 960 of the drilling assembly 850. The second housing 960 is clamped into the first housing 925 that is rigidly soldered to the housing 920 of the control module 860. As shown in this embodiment the sensor 870 includes a resistance controlled polarity switch 970 and a LCZ meter 980.

In operation, the vertical drive motor 900 turns its screw 910 in the arm 950, driving the drill motor 905 up and down by sliding the third housing 945 in and out of the second housing 960, which is attached by a sliding positioning clamp to the first housing 925 and thus to the housing 920 of the control module 860. The drill end of the second housing 960 has an electrically insulating nosepiece that holds three 0.010 inch diameter feet 965 to reference to the nail surface, that are pointed for positive lateral location on the nail.

In testing this drilling device, tests began without the resistance controlled polarity switch 970. A pulsed power supply 975 was hooked through a footswitch to the vertical drive motor 900, with manually switched polarity reversal. The drill motor 905 was simply on-off switched. Some tests were run to see what voltage was best for the drill motor. Fingernail clippings were used, and it was found that there was no drill stalling above 2 V so that supply was set at 2.2V. The motor draws 34-35 ma, no load, at that voltage.

The vertical drive motor 900 was run on single 100 millisecond 20 volt pulses. The pulse voltage was about 4 volts into the loaded motor. The 72 turns/inch screw 910 would move the nut 955 0.014 inch per revolution. It takes 30 pulses to rotate the motor one full revolution. Thus, the theoretical nut travel would be about 0.5-1 mil per pulse. However, the pulse repeatability, or what the motor overshoot/pulse is were undetermined.

Actual tests showed that it took 10-12 pulses to drill through a wet (1 minute hydration) nail clipping with a 0.012 inch diameter drill. This says 2 mils per pulse, and the drill motor current per drive motor pulse went from 35 ma up to 60/70 ma, then settled back to 35 ma. Clearly, the step motion quickly loads the drill motor with the load declining as the drill moves to a no-downforce state into the nail.

On subject's left hand little finger nail overhang, drilling was tried based on the above data. It didn't seem to be drilling through. The downforce from the vertical drive motor 900 being pulsed many times began pushing the drill motor 905 back. Removing the drill bit and inspecting it microscopically, it was found that it was dull. This drill had been used 2 or 3 times. A new drill bit was installed and found to drill properly, moving through a 18 mil thick, dry nail overhang in 5 or 6 pulses (3.5 to 3 mils/pulse). It took 8 or 10 pulses to drill the second hole next to the first one. It would hardly drill a third hole through the same nail. So, the nail dulls drills very quickly.

Hydrating the nail for two minutes seemed to help by reducing the drill motor 905 current variation per vertical drive motor 900 pulse. In the dry instance, the drill current variation was the 35 to 66 to 35 ma over 3 to 4 seconds case cited above. With the hydrated nail, the current variation was 35 to 48 to 36 over 2 or 3 seconds, implying that the drilling took less power and moved through the nail faster.

It was time to try the real test. Using subject's left hand little finger, a new drill was tried on the dry, 17 mil thick overhang, establishing the average 3 mils/pulse rate (peak vertical drive motor current—40 ma). Drilling then began back over the nail bed, letting the vertical drive motor current peak and fall back completely before the next pulse. The peak current was in the 60 ma range, indicating that the drill had already dulled. After six (6) vertical drive motor pulses, the LCZ meter 980 had dropped from 15 meg ohms to 3 meg ohms, but the drill motor current was still 45 or so. Suddenly the drill cut through and into the nail bed. The LCZ meter 980 measured 5-10 K ohms (the resistance through ECG-skin-skin-ECG is 24 K ohms.), it had gone to blood.

Next a new drill was inserted and the nail hydrated by soaking the left hand little finger tip in de-ionized water for 2 minutes. The 17 mil thick overhang drill thru took 5 vertical drive motor pulses, with a drill motor current pulse of 35-45-35 ma over 3 seconds. Going to the nail bed location, the drill motor current pulse was 35-50-35 over 4 sec. After 5 vertical drive motor pulses the LCZ meter 980 was still at 15 meg ohms, so the vertical drive motor was pulsed for the 6th time. The LCZ reading dropped to 3 meg ohms, then subject began feeling a sensation. The drill was backed out, the drill motor turned off, the drill motor/stationary drill stepped back in and an impendence of 14 K ohms was measured. There was no blood at the bottom of the microconduit.

The question of downforce on the drill and vertical drive motor down motion on the drill motor led to putting an electronic dial indicator on the Arm. At approx. 100 mils deflection, the indicator head applies approx. 30 grams of downforce. Below are the measured distances/pulse Up (against the arm downforce) and Down (arm downforce helps)

| Pulse | Up (deflection μm mils) | | Down (deflection μm mils) | |
|---|---|---|---|---|
| 1 | 17 | 0.7 | 85 | 3 |
| 2 | 22 | 1.0 | 99 | 4 |
| 3 | 15 | 0.7 | 97 | 4 |
| 4 | 24 | 1.0 | 120 | 5 |

It was noticed that the Down motion seemed to give two motor steps per pulse (on the rise and fall of the pulse?) while the Up motion—lifting the 30 gram load—stepped only once. Anyhow, the up direction motion is about 30% of the down-loaded direction. This would tend to produce a load for some time against the drill while it drilled into the nail, causing it to drill further than anticipated, because even though there isn't a 30 gram weight on the arm while drilling nail, the weight of the motor, arm and housing would undoubtedly cause it to move farther than in the up direction, where these things are having to be lifted by the vertical drive motor.

The pulser and output pulse electronics were checked. It was found that the pulser was giving two pulses close together for each foot pedal contact. Further adjustment got the pulser to give one output pulse per foot pedal contact. Ten down measurements were then performed, with the deflections ranging from 15 to 75 μm, all probably having to do with slop in the drive screw/nut, friction in the guide tube and the like. The up ten measurements ranged from 5 to 25 μm.

What about real motion while drilling through and backing out of the nail? A 0.018 inch (450 μm) thick nail overhang was drilled through on subject's left hand middle finger after a 2 minute hydrating soak with a new (sharp) drill. The electronic deflection gauge was engaged with the arm near the drive nut. It was moving 25 to 50 μm per step until the drill engaged the nail and began drilling as shown by the drill current measurement jumping up and declining. During the drilling sequence of 6-7 steps the drilled moved 30 to 70 μm per step for a grand total of 350 μm-100 μm short of the measured nail thickness.

Cobalt steel drills were acquired that were coated with Titanium Nitride—a hard coating that is electrically conductive. These cost about ten dollars each, but initial tests drilling through overhang 6 times showed much less wear than with the steel drills used previously. With those, after 4 or 5 holes, it was difficult to force them through the nail and some noise was heard while drilling.

The question of drilling rate/wear on a hydrated nail showed that the motor drilling current was reduced from about 60 ma~2.2 v. to about 48 ma. This implies either water lubrication that reduced friction, or softening of the nail, which reduced its resistance to being drilled. A number of experiments were performed with number of pulses to drill thru an overhang of known thickness and produced quite variable results. The rate ranged from 0.3 mils per step to 1 mil/step. Pull-out was in the range of 8-10 nails per pulse.

The drill motor speed was measured which was in the range of 800 rpm. Increasing the drill voltage to 3 volts (40 ma) increased its speed to about 1500 rpm. Test drillings at this voltage showed improved drilling rate and drill rate repeatability. Quick tests in the overhang showed 1 mil/down step dry and 0.75 mils/down step wet. Using a new TiN coated drill, a dry test was begun in subject's left hand little finger over the nail bed The motor current rose to about 90 ma after each down pulse, and dropped back to 60 ma after having drilled to its maximum depth, after several seconds. Based on previous tests, the drill was pulsed down at a rate that kept the drilling current above 80 ma. It took 16 pulses to drill through nail overhang that measured 17-18 mils, giving a drilling rate of 1.1 mils per pulse (assuming perfect uniformity). Over the nail bed, the LCZ meter stayed in the 14-8 Meg ohm range for the first 11 pulses. It dropped to 100K on the 15th pulse, then to 16K on the 16th pulse. The vertical drive motor was mechanically reversed and the drill motor backed out (while running) in about 12 pulses.

The subject could feel the effects of nail/drill heating during steps 14, 15, 16. It was not terribly painful, but was clearly getting hot. After the 16th step the drill was allowed to run at that elevation and the sensation vanished, presumably because the drill didn't produce heat on or near the nail bed.

Early results show that it works, the heating has to be eliminated either by going to less down motion per step or possibly drilling the nail after hydration, or even fully wet. However, before the fully wet experiment, the nosepiece will have to be changed on the second housing 960 that holds the pointed feet that pin the drill to the nail surface. A plastic nosepiece should ensure that there are no mechanism to drill electrical leakage paths that would invalidate the ohmic altimeter readings.

The metal nose of the second housing 960 was replaced with a Teflon nose to provide good electrical insulation between a possible nail-to-housing resistive leakage path. At the same time 4 BeCu feet were used rather than 3. These are 0.010 inch diameter, sharpened cylinders, approx. 0.130 inch long, inserted in 0.100 inch deep holes in the nosepiece. This leaves them sticking out about 0.030 inch and spaced beyond the 0.075 inch diameter drill clearance hole in a rectangular fashion. This allows them to provide more stability in straddling the curve of the nail.

The experiment with wet drilling of hydrated nails started by using a new drill to drill a test hole in the subject's dry left hand little finger nail overhang. Here the overhang measured 0.017 inch thick and it took 20-23 pulses to drill through it (0.0008 inch/step).

Soaking the finger in water for 3 minutes and adding a drop of water around the drill before starting drilling was tried next. Here it required 15 pulses to drill through the same area. In both cases the 100 ma/step dropping to 60 ma/step procedure was used. So, wet drilling through a hydrated overhang increased the drilling rate to 1.1 mils per step.

Finally, drilling was set up over the nail bed, still using the same drill, hydrated for ⅔ minutes, a water drop was placed on the nail at the drill site and drilling was begun. The first 9 pulses showed no motor current change. The next 2 pulses produced slight fluctuations. The 12th through 28th pulses were done using a Step/80 ma/wait to 60 ma/Step down drive sequence. The fall time was about 1.5 seconds. At the 14th step, the resistance dropped from 1.5 Meg ohms into the 800 K ohm range, then returned to the vicinity of 1.5 Meg ohms. On the 15th step, subject could just detect a heat pulse and the resistance fluctuated downward and back up again. On the 16 Step, the very slight heat pulse was again felt, with the resistance decline and then recovery. At this point drilling was stopped and the conduit examined.

The bottom of the opening was quite pink but there was no blood. The bottom of the hole was probed with a 3 mil diameter tungsten probe wire and the subject could feel the probe when pressed against the holes bottom. Using this probe, the electrical impedance was tested by hooking the tungsten probe to the LCZ meter, sticking it in the hole, pressing against the bottom and measuring the resistance to the ECG electrode stuck to the same finger. It measured 700 K ohms, about the same number as the minimum resistance in the transient resistance change noted while drilling.

This raised several questions. (How thin is the remaining nail membrane at the bottom of this hole? It clearly exists from the resistance measurement (high), plus probing with the tungsten wire did not produce the sharp pricking experience noted when probing holes that had been drilled to blood. Would a residual thin membrane be permeable enough to permit successful drug delivery such as for fungal treatment? Also, one wonders if the sensation detection nerve net under fingernails is more sensitive/dense than the one that exists under toenails. It seems that with the fingernail, the subject's detection of sensation is earlier and more acute than when microscissioning a larger opening in another subject's toenails. This can only be tested by a test drilling of one of the first subject's toenails. It is necessary to get the resistance-detecting drive motor reversing circuit working to eliminate the need to view the drilling action.

The tip of the drill extends about 0.004 inch out from its body's maximum diameter. This suggests that if subject can feel the drill and wire probe, the hole bottom is probably within 0.004 inch of the nail bed in its center. Perhaps a flat, endmill end would work better, and give a more uniform bottom thickness. A 0.032 inch carbide endmill was tried and it worked fine on an overhang.

An even smaller inexpensive electric motor was found that should be incorporated into further experiments.

| Existing Large Motor | New Smaller Motor |
| --- | --- |
| 0.250 inch od, 0.650 inch L, 0.800 inch OAL | 0.185 inch od, 0.4 inch L, 0.625 inch OAL |
| 875 RPM @ 30 Ma, 3 V | 1200 RPM @ 35 Ma, 3 V |
| 2100 RPM @ 43 Ma, 6 V | 2300 RPM @ 45 Ma, 6 V |
| 4500 RPM @ 35 Ma, 10 V | |

Experiment 2

Auto-Stop/Reverse of Microconduit Drilling

In order to move on to the Resistance Altimeter experiments, a comparator/relay circuit was fabricated to sense the ohmic resistance from the drill bit through the finger/toe to a nearby ECG patch adhered to the hand/foot. By using a relay and an amplifier/comparator chip, a potentiometer reference can be adjusted to essentially set the electrical resistance trigger ohmic value to flip the relay. The relay is hooked to a reversing relay (DPDT) to reverse the vertical drive motor. Thus, nail drilling is begun by stepping the vertical drive motor to move the drill motor down, pressing the spinning drill against the nail. As drilling proceeds, a depth is reached where the drill bit-to-body-to-ECG electrode electrical resistance begins to drop from about 3-6 meg ohms toward 100 K ohms, on down to the 10/20 K ohm range as the drill bit moves through the nail and into the increasingly living nail bed structure. At whatever predetermined electrical resistance trigger value has been previously set, the reversing relays are energized, the vertical drive motor reverses and the spinning drill is lifted away from the bottom of the hole it has been drilling. Naturally, the idea is to get close to the nail bed, but not to drill into it significantly (meaning to pain and blood), in a highly repeatable, no-judgment-needed, manner.

Figure 8:
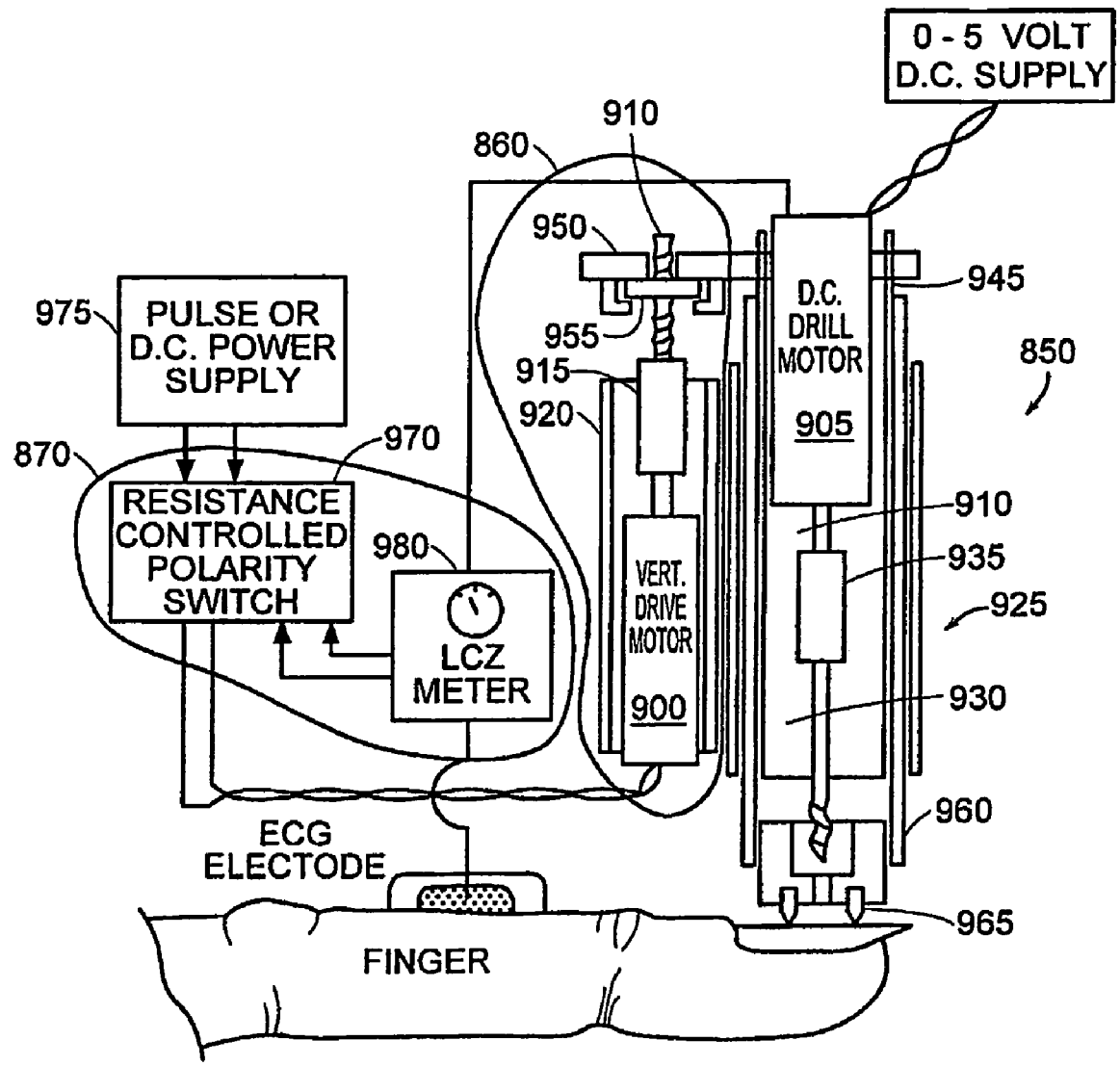
FIG. 8 is an illustration of an embodiment of a small drill arrangement to permit controlled drilling of a nail by referencing to its top surface.

FIG. 8 is a block diagram of this arrangement. A more complete circuit diagram is shown in FIG. 9. Several considerations had to be met. The first problem was that even though the circuit could sense micro amps of current and flip the relays, as soon as the drill began withdrawing, the resistance would go up and the relays would flip back, causing the drill to be stepped down. A resettable latch was needed so that once triggered, the drill motor would be withdrawn further with each foot pedal pulse input, regardless of the resistance increase back up to about 5 meg ohms once the drill was out of the hole. Once the operation was over, step motor pulsing was stopped. Then a pushbutton could be pressed to set the system back so that the next input pulses would drive the drill motor down again. The details of this latch are explained herein below.

Also, a manual reversing switch was needed. In drilling nail overhang or partially through the nail, where the resistance will never drop into the trigger range, it is necessary to easily reverse the vertical drive motor. Again, a pushbutton was installed to give a pulse to the input that will flip the relays into reverse. Returning to the down direction can be effected with the resettable latch pushbutton, the two switches allowing manual up/down control.

Finally, the question of easy drilling was explored. It was found that dehydration/degreasing followed by several minutes of hydration softened the nail overhang considerably, reducing the pulse count for going through a 0.017 inch thick nail overhang from 20 dry to 10 hydrated using the Ti Nitride coated drill. It appears that an acetone rinse followed by a methanol rinse dries and degreases the nail, so that a several minute water immersion hydrates the nail more than without the solvents.

The circuit schematic of FIG. 9 shows details of all the main electrical controls. At the top center is the ECG Pwr supply 1200. In order to eliminate the anodic-cathodic effects of D.C. current through organic tissues, an A.C. power source is used. Here it is a 1.5 volt battery 1205, current limiting resistor (25K) 1210 and three series diodes 1215, to hold the voltage at approx. 0.8 volts. This is connected to relay 1217 that is energized by a 500 C.P.S. oscillator 1220. This A.C. supply is hooked to the ECG electrode stuck to the skin near the nail being worked on to supply current to effectively measure the through skin/interior/nail bed and drill resistance that eventually triggers the reversing circuit once the high resistance nail material has been removed from the hole. The manual polarity pushbutton 1225 at the input acts to reverse the motion of the drill motor.

At lower center is the resistance sensing circuit 1202. Resistor Rf 1230 across U1 1235 sets the range within which the trigger resistance permits enough current into U1 1235 to trigger the relays 1245, 1250. The potentiometer 1240 acts as the vernier to adjust the trigger point for a certain Rf 1230. For instance, a trigger resistance of 50 K-65 K ohms can be set by the pot with an Rf of 249 K ohms (150 K ohms changes the trigger range to 25-33 K ohms). The output of the first relay 1245 energizes the reversing relay 1275 on the right. The momentary push button 1260 unhooks the Latch function. When the second relay 1250 closes on the circuit triggering, it grounds the output of U2 1255 through the normally closed push button. U2 1255 is already at ground and would go up when the input resistance rose as the drill pulled away from the nail bed. However, it can't, being held at ground, so the relays cannot open. Pressing the momentary push button 1260 unhooks U2's output from ground, opening the relays. U2's input is calling for a high output, so the vertical drive motor will begin driving the drill down again with input pulses.

On the right is the polarity switch 1204. The vertical drive motor 1280 is pulsed by the foot switch 1270 triggering a pulse supply 1295, driving the drill downward. Once a microconduit is drilled in the nail and the impedance (resistance) drops sufficiently to trigger the relay 1275, a large reversing pulse is put across the vertical drive motor 1280. By discharging the 2200 μfd capacitor 1285 thru the motor. The vertical drive D.C supply 1290 provides this 12-15 volt charge.

Once all of this was working, the resistance to use as the trigger resistance below which the downward drilling drill would be pulled upward and away from the nail needed to be determined. The ECG electrode to ECG electrode resistance is in the 60 K range (about 30 K each). If it is assumed that one would like to stay on the not too deep side on the drilling and it is believed that 20K drill-to-bed resistance would do this, then, using resistors between the ECG Pwr 1200 and the input to Drill 1265, the Rset pot 1240 is set to trigger at 51 K input resistance (equivalent to 30K ECG+21K nail/bed resistance).

Next, subject's left hand little finger nail was dehydrated with acetone and methanol rinses and the nail hydrated for 5 minutes. Drilling the overhang required 9.5 pulses after initial drill firm contact as determined by the drill motor current rising from 40 ma unloaded to 60/65 ma with light load. A drop of water was placed on the nail around the drill bit. In the drilling sequence, the vertical drive was pulsed once using footswitch 1270. The drill motor current rises to 110/120 ma, then declines to 65-70 ma after a few seconds at which point the vertical drive was pulsed again. In the case of the overhang, complete penetration is indicated when the drill motor current drops rapidly to 60 ma. Also, the water can be seen to drain out through the now-open hole, which doesn't happen over the nail bed.

In the test over the nail bed, the nail (now only one side is exposed to the liquids) was again dehydrated and hydrated it for 5 minutes with de-ionized water. The drill feet were set on the nail so the drill would be about 0.050 inch back from the delineation line between the nail on the bed and the nail in overhang mode.

Drilling was begun and after 8+ steps, the drill began rising out of the borehole. There was absolutely no sensation. Probing with a fine wire (0.007 inch diameter Tungsten Wire) showed that the hole bottom was rigid. Pushing down on the wire a bit in the hole center forced it through the remaining nail membrane and subject could feel moderate sensation.

Interestingly, the 8+ steps indicate that the drill went through the nail over the bed quicker. As the drill was once-used, if anything it would be slightly duller than when it drilled the overhang. Since hydration of the back and front of the overhang took place, it might be thought to be softer? The implication is that either the nail over the bed is thinner than 0.016/0.017 inch thickness of the overhang or that it is softer—perhaps as one nears the nail bed, or that the drill went further in the overhang because it drilled all the way through. The depth resolution of the pulse-counting is 1.7 mils/pulse in the overhang, and assuming the same thickness over the nail bed it is 1.9 mils/pulse.

After the first test, a number of modifications were made to the electronics/switches to make life easier. Remote push buttons were installed to permit use of a trigger resistor to simulate the drill electrically connecting with the nail bed. Unlike a simple switch on the up down relay, this does reverse the drill motor direction while also testing the circuit functionality. Second, the latch reset push button was placed near the drill site. Both push buttons were located to allow actuation while looking through the microscope. Finally, the circuit had a couple of intermittent connections in the solder joints/wires, which were eliminated to assure reliable operation.

Using fixed resistors, the trigger resistance was changed from 51 K ohms to somewhere between 30 K where it did reverse and 33 K where it didn't. As before, acetone followed by methanol on were used on subject's left hand little finger to degrease and dehydrate the nail. This was followed by a 10 minute water immersion to hydrate the nail. The 0.017 inch thick overhang was drilled, in a water drop, in 9.5 down steps, about the same as previously. Hydrating the nail for another 5 minutes, Drilling was moved further toward the quick behind the previous hole. This took 7+ steps, rather than the 8+ before. The drill backed out and there was no sensation whatsoever. The bottom of the drill hole was pressed on with a blunt needle and could clearly be felt as soft with the blunt needle as well as the subject feeling the needle pressing through the just-drilled little finger. It was pink with absolutely no blood.

Figure 10:
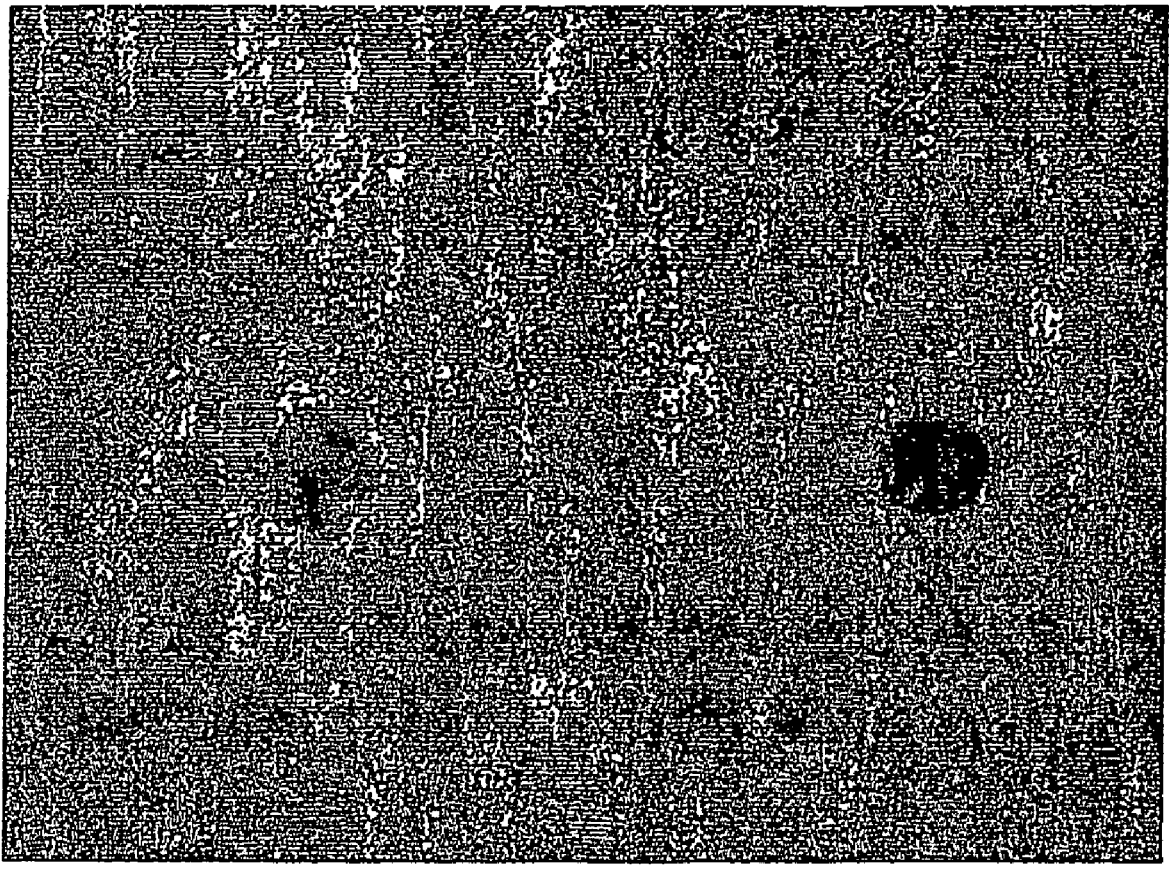
FIG. 10 is a photograph showing two drilled holes in the subject's left hand little finger nail. The left side hole was drilled using the 51 K ohm trigger resistance. The right side hole was drilled using water on the nail.

FIG. 10 shows two drilled holes in subject's left hand little finger nail. The left hole was drilled using the 51 K ohm trigger resistance, discussed above. The right hole was drilled as reported above. The three dashed lines top to bottom between the two holes follow the slight color change showing the demarcation line between the nail bed on the right and the overhang on its left. The left hand hole was drilled, as described above, using 51 K ohms as the trigger resistance. The top right hand half of that holes bottom is visible, while the lower left hand half shows where the wire broke through the nail membrane. The right hand hole was drilled using a 30 K ohm trigger resistance setting, meaning it should be deeper, and its bottom is uniformly pinkish and subject can, feel a wire probing it all over its bottom, indicating there is little or no nail membrane left. Measuring the hole depths with a tungsten probe tip that was marked off to serve as a ruler showed that the 51 K ohm hole was 15.5-16 mils to its bottom, while the right hand (30 K ohm) hole was 19.5 to 20 mils deep.

With this data, the next step was to calibrate the feedback resistor (Rf size vs. the 2-8 volt swing available for Rset vs. the resistance at which the vertical drive motor would reverse. It was found that 100 K ohms gave the best range. The table below shows the Uset voltage and the resistance that triggers the reversing process.

| Rf = 100K ohms Uset 2 v. | 62K ohms | No trig. | 58K ohms | Yes trg |
|---|---|---|---|---|
| 3 v. | 56K | No | 39K | Yes |
| 4 | 33K | No | 30K | Yes |
| 5 | 30K | No | 22K | Yes |
| 6 v | 22K | No | 19K | Yes |
| 7 | 17K | No | 15K | Yes |
| 8 | 15K | No | 13K | Yes |
| 9 | 13K | No | 11K | Yes |

Ranges for other Rf feedback resistances and the kind of ranges they provided are

| Rf = 249K ohms | 2 v | 133K | No | 110K | Yes |
|---|---|---|---|---|---|
| | 9 v | 37K | No | 30K | Yes |
| Rf = 200K | 2 v | 100K | No | 94K | Yes |
| | 9 v | 37K | No | 30K | Yes |
| Rf = 150K | 2 v | 78K | No | 71K | Yes |
| | 9 v | 22K | No | 15K | Yes |

It is assumed that subject will begin feeling the drill somewhere in the 20-30K range, so the 100K Rf gives ample range either side of that.

In order to set the trigger resistance reasonably precisely, a pot (variable resistor) was used and the Rset voltage set through trial and error around a trigger resistance of 25 K ohms. Once it got close, the resistance of the pot could be increased by 1000 ohms, tested for triggerability and so forth. Finally 25.1 K ohms was settled on, that is it didn't go in reverse at 25.2K but did at 25.1 K ohms, thus getting into a 1000 ohm uncertainty range (5%). Again, on subject's left hand pinky, 3 acetone rinses, plus 3 methanol rinses, plus a 9 minute submersion in de-ionized water were used. A test drilled was performed on the 17 mil thick overhang that took 8+ down pulses to go through, a bit faster than before.

The nail bed was then drilled into behind the 30 K ohm-33 K ohm hole shown in FIG. 10. In both cases the area around the drill was flooded with water. At 7 pulses, subject felt a slight sensation. At the eighth pulse the sensation became stronger, nearing pain. The drill reversed direction—implying 25.1 K ohms had been reached. Microscopic inspection showed the hole bottom to be quite pink, however there was no blood, not even any blood seepage after several minutes. The depth measurement showed this hole to be 20.5-22 mils deep, and subject could feel the touch of the ruler tip quite easily. This appears to imply that the nail bed was drilled into, but clearly not far enough to hit the capillary region. So, it appears that about 25 K ohms is the depth limit on subject for sensation.

One interesting fact about the experimentation on drilling subject's finger nails, subject has never covered or otherwise protected the drilled nails, with the holes often becoming filled with grease, crud and general detritus. However there has been no sign of infection in any case. Further, whenever drilling has gone deep enough for subject to experience strong sensation or even clear-cut pain, all sensation disappears within 60 seconds. Finally, pressing down hard on the drilled nail produces no different sensation than with a non drilled nail In the next experiment, a hole was drilled to a depth set by a trigger resistance of 28.1 K ohms-28.3 K ohms. Using the acetone, alcohol, de-ionized water hydration sequence along with drilling in a de-ionized water drop on the nail. Drilling went through 6 down steps. On the 7th pulse subject felt sensation that increased as the bit drilled on. On the 8th pulse the down-drive motor backed the drill out. The sensation was not great, but clearly increasing. It was not as near-pain like as in the 25 K ohm trigger resistance case. The depth was measured and found to be 18-19 mils deep. The bottom was stiff, clearly indicating a thin nail membrane, but probing it produced a distinct pressure sensation, again not as intense as probing the bottom of the 25 K ohm hole.

A review test of subject's skin and ECG resistances was carried out. Using the LCZ meter at 1 volt and 1000 cycles.
  2 SS probes in to slight pain 30 K ohms
  2 ECG electrodes on skin=3.3 K ohms
  1 SS probe+1 ECG to slight pain=20 K ohms
  1 SS probe+1 ECG to strong pain=4.6 K ohms This gives a baseline of resistances that demonstrates them to be nearly an order of magnitude lower than the 31 K ohms previously determined. It is uncertain whether one should add about 4 K ohms to the trigger resistance set up to account for these kind of constant offsets. It is decided not to because the trigger resistances are simply depth indicators, which must be calibrated by tests.

So, the same experiment as before was set up, to reestablish a crude calibration. Again, using a variable resistor, the trigger was set to occur between 31K and 32.5 K ohms. Using the standard hydration sequence, along with a new ECG electrode and the a.c. power supply drilling began thru a water drop on the nail. At 7 down pulses, pulsing was stopped with the footswitch and the drill was allowed to move deeper simply from the diminishing loading of the 7th pulse. Just at the moment when subject thought he could feel something, the circuit tripped (a voltmeter was on the reversing relay) and the down motor went into high speed reverse backing the drill out.

The hole measured 0.016+ mils deep (as opposed to the 18/19 mils for the 28 K ohm trigger case or the 20/22 mil depth of the 25 K ohm trigger disclosed above. Another interesting factor is becoming apparent. In each of these examples, subject could feel a probe at the bottom of the drilled hole shortly after drilling as the hole depths were measured. In going back days later, all holes to date have had hard bottoms, and subject cannot feel a probe pushing on any of these hole bottoms. It is quite likely that this can reveal the transition tissue thickness. Assuming that the nail gradually goes from a dry, hard state through an increasingly soft and wet state until some point where this transition tissue becomes the epidermis, perhaps without a stratum corneum. Since the drillings have not gone to blood (implying the dermis) in these tests, it seems that for a 15 mil overhang, the 31 K, 16 mil depth is near the top transition to hardness, and the 25 K ohm, 21 mil depth is near the epidermal region—especially since clear liquid was seen in its bottom. That means that the transition region is about 5 mils thick. A fungal infection probably lives in this transition material, since it is adequately wet. Also, the fungus and its by-products are responsible for taking up more space, pushing the nail away from the body and producing the considerable thickening of the under-nail material reported previously.

Experiment 3

Drilling Dry vs. Wet Nail

A couple of test drillings began through subject's left hand pinky overhang which measures 16-17 mils thick. Using the same drill that was reported on after approximately 12 drillings, the first experiment was to simply drill through dry and see how many down pulses it took (the drill motor was running at 10 volts.). Drilling ended after 40 down pulses, the hole was partially through (est. 10 mils) and had a black bottom.

The next test was to use the same drill and hydrate the nail in the standard way (3 acetone rinses and blow-dry, 3 methanol rinses and blow-dry, 10 minute $H_2O$ soak). Again, although drilling in water, drilling ended after 50 down pulses. Here the hole was slightly deeper, not black on the bottom, but not through.

During both tests, it was noticed that the motor current never exceeded about 90 ma, where it usually pegs the 100 ma meter after each down step. This implies a really dull drill that is wearing, rather than cutting, its way through. However, in the work over the nail bed, the soft transition region hypothesized previously may have allowed the drill through the last 5 mils more easily.

Another series of experiments was begun using a new drill. Beginning with the full-tilt hydration and an 10 volt drill motor supply, it was found that 6 down pulses about every second went through 16 mils of subject's left hand pinky. Microscopic inspection showed essentially no wear between the unused condition and after drilling.

Next, the nail was allowed to dry for 1.75 hours and dry drilling tried. After 16 down pulses, drilling stopped but the drill hadn't passed through the nail. The drill looked as sharp as after the hydrated drilling above. The was set up drill up so it could be seen through the microscope used for observing the process, the voltage turned down enough so it was turning slowly and it was discovered that it was running backward, how long has that been going on. The wires are color coded and were proper. It may have been several weeks.

The power polarity was reversed to turn the drill in the right direction for drilling, another dry hole was drilled in 4-5 down pulses. The drill motor voltage was turned down from 10V to 7.5 volts and it took 5-6 down pulses. The drill was inspected and one can now just see wear on the cutting edges, but the line between the inclined planes forming the tip is as sharp as when unused.

Next, the same nail was hydrated as usual, the drill was run at 10 volts, and it went through the left hand pinky overhang (17 mil thickness) in 1.8-2.2 pulses. The tenths are unjustifiable, but it was pulsed once, a second later pulsed a second time and it immediately went through. (subject knows the drill has come through the overhang by feeling the drill come against his under-nail skin. Also, the water surround around the drill quickly leaks away through the opened hole.)

Inspection of the drill at high magnification now shows a discernable brightening of the drills cutting edges. An unused drill shows a zero dimension sharp edge. This brightening is interpreted to be the beginning of becoming dull.

As a second reference point, the drill motor voltage is reduced to 7.5V, (the no-load current was 35 ma rather than 45 ma at 10V). Hydrated as usual, drilled through subject's left hand pinky overhang (17 mils in this location) in 2.5-3 down pulses. The max current was about 100 ma, declining to 75 ma within a second. This drilling took place after 7 drillings, making it the 8th hole drilled. Drill wear still seems minimal. This much faster drilling may well be more repeatable and probably generate less heat.

The trip resistance was set up for 30 K ohms and a standard hydrate of subject's left hand pinky was performed. Using an ECG electrode between the back knuckle and hand on the left hand pinky, it was put under the drill, a water glob placed on the nail and drilling (7.5 v) began. The first down pulse raised the drill motor current from 35 ma to 60 ma. The second pulse raised the drill motor current to 100 ma and the same for the 3rd down pulse, each of which were about 2 seconds apart. The 4th down pulse produced a slight sensation before the down drive motor reversed and yanked the drill out. There was no sensation of heating. The sensation before reversing was a slight pricking feeling. There was no color in the drill hole bottom, but poking the bottom with a probe produced a pricking feeling. The bottom was slightly soft. After a day, probing again showed the bottom to be firm with no sensation noticed.

Next, it was decided to repeat the above experiment. Because the fast extract circuit was not turned on, stepping down with the foot switch in the wet, hydrated nail proceeded in too deep because the last down pulse (#4) drove the drill into blood. (Remembering that the next foot switch down pulse would extract the drill a step at a time, the reason for the instant, d.c. reversal on the vertical drive motor). The sensation was sensible, but not intense. Anyway, drilling was relocated, the non-rotating drill stepped to the nail, then backed up one step, and puddle of water was placed on the nail. Turned on the drill motor and stepped the rotating drill toward the nail. As soon as it hit the water, just touching the surface of the nail, the vertical drive reversed and backed away. This indicated a very simple problem. If drilling wet, the slight bleeding from the nearby hole contaminates the water and the drill senses the neighboring holes resistance through the shunting bloody (or even clear fluid?) water. So, one can't use a water puddle on the hydrated nail when drilling multiple holes near one another.

Everything was then blown dry—drill chamber, nail, etc. and the hole drilled dry. It worked fine, took 4 down steps, maybe there was sensation, the vertical drive reversed at 30 K ohms, and the hole was similar to those discussed above, about 18 mils deep, no color on the bottom, soft bottom, probe could be felt by the nail bed.

This implies that one must drill a hydrated nail, but use no water on it during drilling due to bodily fluid contamination of the water causing a shunt to adjacent openings, which the drill will sense and reverse away.

Experiment 4

D.C. Drive System

The next step was to attempt the simplification of the vertical drive system. The use of pulsed vertical drive may well be unnecessary considering the sensitivity and rapid response of the impedance measuring/control system. It was decided to use direct current to power the vertical drive motor (It was already being used on the rapid reversal to extract the drill). If there was enough torque, a constant down force could be set on the drill and the spinning drill could still be rapidly withdrawn from the hole once the preset nail bed resistance value had been reached. Experiments showed that more than enough down force could be achieved with 1-2 volts on the vertical drive motor driving a 72 thread per inch screw/nut combination in the drill motor motion arm.

Figure 3:
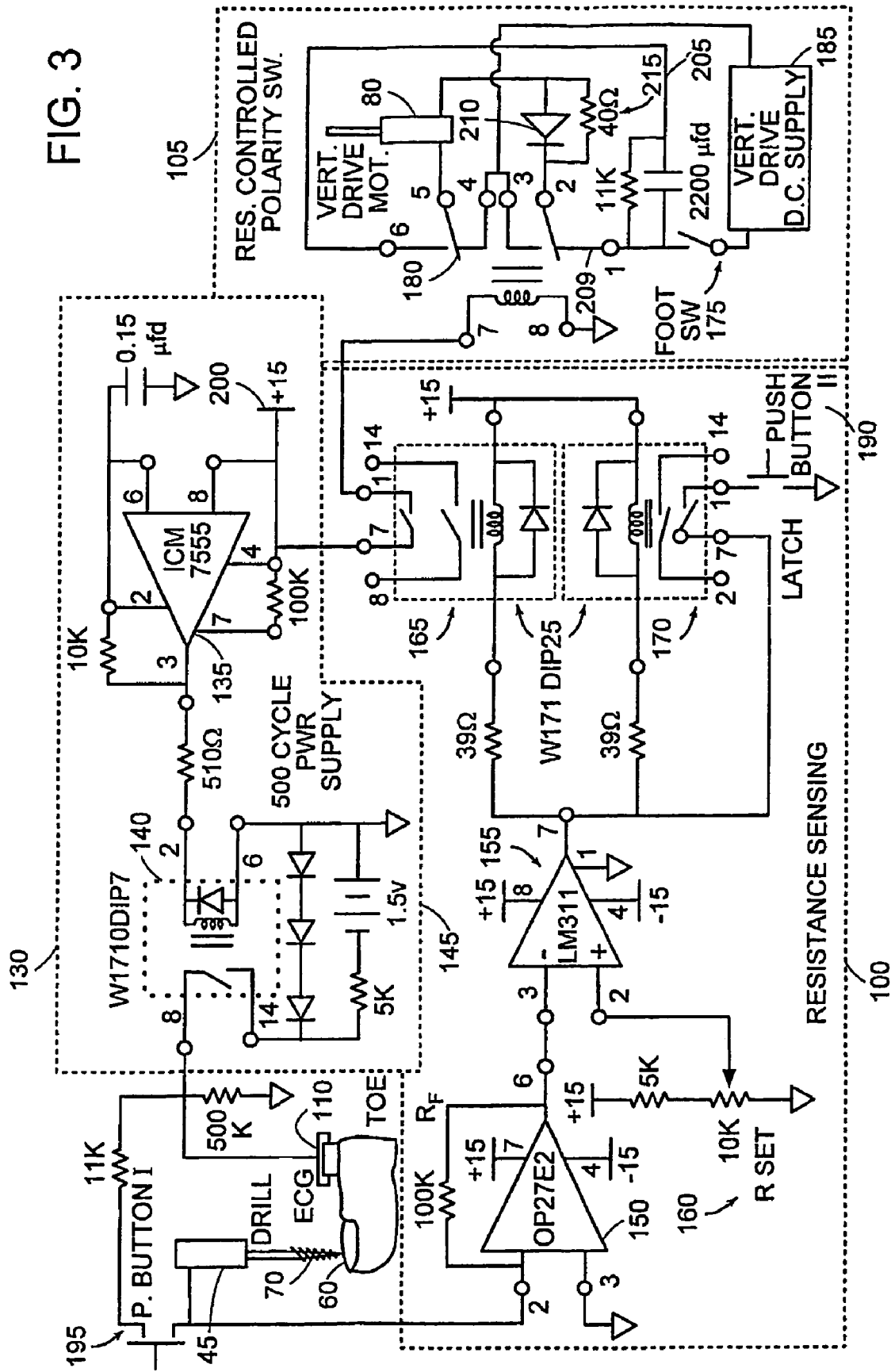
FIG. 3 shows a preferred circuit for measuring resistance for use with the impedance sensing drill of FIG. 1.

The preferred schematic, as seen in FIG. 3, shows the new circuitry around the double pole double throw relay 180, with the pulse supply (1295 in FIG. 12) replaced by a D.C. power supply, 185, a diode 210 and a resistor 215. The relay acts to reverse the polarity from the D.C. Supply. When fully charged, the 2200 µfd capacitor 205 and 1 K ohm resistor 204 produce a pulse of sufficient amplitude to give the vertical drive motor a 3 revolution reversing kick to quickly and fully pull the drill out of the hole drilled in the nail or skin. The Diode 210 isolates the motor from the full voltage during the down drive action, allowing the 40 ohm resistor 215 to determine the voltage for applying the down force. With the D.C. supply set at approximately 10 volts, the vertical drive motor voltage is approximately 1.5 volts to achieve adequate down force on the drill during the drilling process.

With the above conditions and 4 volts, 60 ma on the drill, it takes approx. 3 seconds to drill through the 0.023 inch thick overhang of subject's non-hydrated left hand index finger.

The drill system as seen in FIG. 8 is placed against the nail, with the pointed locating pins (feet) in the Teflon nose piece of the drill motor housing pressed into the nail surface for location stability. With the drill running, the foot switch is pressed, turning on the vertical drive motor, which moves the drill motor housing/drill down against the nail. With the foot switch pressed down, the vertical drive motor continues to apply stall torque to the drive screw, forcing the spinning drill into the nail. Once the thru-drill to body to ECG electrode electrical resistance drops to the predetermined value, the trigger circuit switches the double pole double throw relay, reversing the connections to the motor. This discharges capacitor C, producing a fast-rise reverse polarity pulse on the vertical drive motor that lifts the drill out of the hole in the nail.

In another experiment under the same conditions as reported above, subject's fully hydrated left hand pinky overhang (0.017 inch) was drilled through in 1 second. This time can be adjusted by varying the voltage on the vertical drive motor. With the previous pulse system, the number of pulses was being counted in the experiments discussed above, and recall that the time per down pulse footswitch actuation was on the order of 2-3 seconds. There is also the difference in drill motor parameters from then it was 7.5 volts and 35 ma no load, where now it is 4 volts and 60 ma. The former power supply stopped functioning, perhaps indicating that it was somehow current limited then. In any case, the pulsed approach did not put a constant down force on the drill—it was maximum after actuation and dropped off as the drill moved into the nail (this was evident in watching the milliameter). So, the d.c. vertical drive motor arrangement certainly drills faster, presumably due to applying a constant down force. After several experiments to set reasonable drilling times and fast extraction, the resistor-capacitor circuit is 2,200 micro farads, 1 K ohm and the D.C. Supply voltage for the vertical drive motor to function is 12 volts, with the diode shunt resistance at 40 ohms. This produces a high enough down drive stall torque to move the drill into the nail well, and the capacitor discharge is ample to reverse the vertical drive motor and yank the spinning drill out of the hole in a few milliseconds (guesstimate) once the trigger resistance has been reached.

Some tests were run on a fake fingernail consisting of 0.004 inch thick Teflon on top of 0.004 inch thick copper, all taped to a 0.030 inch thick Teflon strip. This allowed drilling through the thin, insulating top Teflon down to the copper conductor that was hooked electrically to what would normally be the ECG electrode circuit input. Tests on this fake nail revealed that soft end stops were needed on the drill arm. Otherwise it could jam into the drive screw holding collar in the down mode (drilling), and fly right off of the screw open end in the up (pull out) mode. Some small diameter, soft, plastic tubing was attached to the vertical drive superstructure to catch and stall the vertical drive motor in the down mode, and just stop the upward motion as the drive screw backed out of the captive nut in the drill motor housing arm. This produced reliable up/down motion without jamming Final preliminary tests were done by drilling through subject's left hand pinky overhang that was sitting on a curved metal screw head, cantilevered in a way to protrude back under the overhang. Thus, the overhang could be drilled through and the drill would touch the metal support, which was hooked electrically to the ECG trigger circuit input. These tests helped finalize the size of the capacitor, 205, to assure ample reverse torque in the vertical drive motor.

In the real experiment, the drill arrangement was moved back over the nail bed and after the standard 10 minute hydration, subject's left hand pinky was drilled over the bed. It took approx. 3 seconds and the drill was yanked out essentially instantly. Subject could just feel something, suspected to be heat related, drilling was not into a water puddle, but only the dry, recently hydrated nail. The trigger resistance was set at 30-31 K ohms, and the hole bottom showed the normal bed whitish/pinkish color, with no sign of clear fluid or blood. Probing the hole bottom showed it to be soft, and subject could feel the probe against the upper nail bed.

It was likely that the drill was becoming dull. It had been used to drill a couple of dozen holes in subject's nails, plus the same number of holes in the copper/copper fake nails, plus a couple of times drilling down to the steel cantilever under subject's nail overhang in the preliminary tests. Additional experiments will have to be conducted with a fresh drill to see whether the suspected heating effect is reduced.

Experiment 5

Use of Endmill in Drilling

Additional applications were considered and tests conducted as follows: There exist small endmills as well as drills. A standard drill has two cutting edges lying at the end of the drill flutes but tilted at an angle up to a near-point as if on a virtual conical surface and 180 degrees apart. As with a drill, the endmill arrangement also has flutes ending in cutting edges. However, these edges lie in the plane of the flat end of the endmill. This arrangement should lend itself to removing the stratum corneum from the skin using the same body electrical impedance end point detection system as cited throughout these experiments. The endmills lack of a point eliminates the hypothetical chance of the point piercing not only the stratum corneum but also on down into or through the epidermis into the dermis and causing pain sensation. Further, there may be a secondary end stop with the endmill. The stratum corneum is relatively hard compared to the underlying epidermis, which is gelatinous. Flat endmills do not work well on soft, spongy materials, so in this case it would tend to stop or slow its removal process once the stratum corneum has been cut off.

Another potential application is on nails. It should drill the reasonably hard nail and open the nail bed fully as opposed to a pointed, twist drill. The pointed drill will produce an opening at the nail bed that is conical, deeper at its center than at its edges. Thus, the chance of leaving thin nail around the periphery of the drilled hole is higher and the delivery of drugs or medication might be reduced near the periphery. The flat bottom produced by the endmill would theoretically leave a more uniformly open nail bed for better drug delivery.

As described above, a 0.010 inch diameter tungsten carbide endmill was used in the sensitive drill modified to make electrical contact with the drill quill that holds the drill chuck, which holds the endmill. With the Stanford Research 5R720 LCR meter set at 1 volt and 1000 cps, and hooked between an ECG silver/silver chloride electrode (AccuSensor 510-005 stuck to subject's left, inner wrist an inch from the thumb) and the sensitive drill electrical connection, the spinning endmill (approx. 1500 rpm) was pressed against subject's left inner wrist about 3 inches back from the center of subject's palm. The initial resistance was 5-7 Meg ohms. After about 5 seconds, the resistance had come down to 100 K ohms, then quickly on down to 20 K ohms, where drilling stopped, assuming from past experience that drilling was well through the stratum corneum. There was nothing resembling a sensation of pain. The sensation was the same as lightly pressing a blunt, worn pencil lead against the skin, i.e., one of something pressing against the skin.

Verification of this was done first by microscopic examination. The outline of a round opening in the generally transparent stratum corneum could just be seen. There was no liquid visible nor was there any reddening or swelling of the skin around the site. Removal of stratum corneum was tested for by placing two ECG electrodes about an inch apart on subject's nearly hairless left hand inner wrist in undrilled locations and measuring the electrical resistance (impedance) as previously discussed. The resistance was 4.1 K ohms. An ECG electrode was then placed over the site just drilled and the resistance was 2 K ohms. This demonstrated that the stratum corneum resistance between an ECG electrode and subject's interior had been essentially eliminated, proving the throughness of the drilled microconduit. This process therefore lends itself to improving electrical contact to the body's interior. It is also possible that one can introduce chemicals into the body through a closely spaced group of these stratum corneum-less openings.

The overhang of subject's left hand pinky nail was then drilled through with the 0.010 inch diameter carbide endmill. The nail was not hydrated, nor was electrical resistance measured. It worked the same as with a drill, going through easily. The assumption was that the resistance drop would be detected and drilling was performed to make sure it drilled well.

Following these proof of concept experiments, some 2-flute micro endmills were ordered: 0.010 inch, 0.015 inch, and 0.020 inch in diameter from Performance Micro Tool, Inc. of Janesville, Wis. Unfortunately, they only come with 0.125 inch diameter shanks, which meant a new collar needed to be made (the drills used in the earlier work had about 0.039 inch shanks). Also, the shanks were 1 inch long, as were the drills, and had to be cut off. However, being made of Tungsten Carbide, diamond abrasive wheels were needed. The machining took a couple of hours, even with diamond, to cut off and also grind the shank end away left and right of the centerline, to produce a thin (approx. 0.020 inch) bar across the shank end to key into a slot in the collar.

A second motor was used on which to mount the collar, as the entire motor/collar/endmill (drill) are easier to replace in the system than taking the piecemeal approach. Experiments with a 0.020" endmill showed that its very sharp flute ends tended to grab in skin replicas such as Teflon and stall the motor. Even with the minimum workable torque possible in the down drive, it tended to push the endmill in to soft materials too fast, stalling the motor. (This didn't happen on the harder nail test.) It was discovered that by running the drill motor at 5-7 volts (100 ma), the stalling could be reduced, but not eliminated. A compromise was to place the end of the endmill very near the surface to be removed and use high motor current. This way, when the down drive was actuated, the distance moved before cutting was minimized, as well as the endmills velocity of approach and it would cut through softer materials without jamming.

It also became apparent during these tests that a new Teflon nose piece would be needed for use on the skin. The sharp pointed feet on the nosepiece could be felt when pressed against the subject's stratum corneum, and they were deforming subject's skin at the site of the endmill touchdown. It would be desirable to have subject's skin flat and stretched taut for uniform stratum corneum removal. A nose piece of Teflon was made that had a 0.187 inch diameter hole through it to clear the endmill, shank and all. Also a ring was machined in the otherwise flat end of the nose piece, that protrudes out from the otherwise flat nose piece end by approx. 0.100 inch. Its inner diameter tapers from the 0.187 inch hole diameter at its base outward to approx. 0.210 inch at its open end. The open end is about 0.025 inch wide before dropping straight down 0.100 inch to the flat nose piece, which has a 0.390 inch diameter. Thus, when pressed against the skin, the protruding ring presses into the skin, pulling the skin taut (like a drum head), and if pressed harder, the skin inside the annulus of the 0.187 inch hole bulges further into the hole. An example of this embodiment can be seen FIG. 2.

The holding arrangement for everything was repositioned to permit presenting subject's left inner wrist to the nose piece of the motor-drill assembly while being able to view the proceedings through a microscope. In setting up the position of the housing, that holds the end piece, to place the end piece ring end below the end of the mill, and testing by pressing subject's wrist against the assembly with the mill stationary, it was noted that the ring on the end piece indented subject's skin and left a circular dent. Also, it could be seen where the endmill had left a small mark. So, the end piece was moved further down relative to the mill's end. Now no mark in the center of end pieces circular dent. However if subject pressed wrist a bit harder, a mill mark was to be seen in the center of the circular dent. An experiment was then attempted.

Instead of moving the endmill motor down, why not press subject's wrist harder, bulging the skin surface inside the end piece circular ring higher up and thus closer to the endmill? After all, once the mill had removed the stratum corneum, the resistance would drop, the down drive motor would yank the endmill away and, this was tried and it worked beautifully. With the endmill motor running, subject's inner wrist skin was pressed against the end piece, then a little harder, then the trigger resistance was reached, the endmill yanked away, and subject didn't feel a thing. Tried it again and it didn't work. Examination of the endmill's cutting end showed stratum corneum hanging from the edges, reducing sharpness and it didn't cut. Cleaned off the stratum corneum and repeated a second time. Again no sensation, fast pullback and a nice round, red hole in the stratum corneum.

Why the first opening took 5 days longer to disappear than the second is unknown. Perhaps it was deeper. As a reference, all the openings are 0.020 (500 am) in diameter, regardless of the image size.

The next set of experiments will attempt to use a 0.010 inch (250 μm) diameter endmill. These carbide micro tools from Performance Micro Tool of Janesville, Wis., are available down to 0.001 inch (25 μm) in diameter. The spiral flute length increases from 0.003 inch length for the smallest diameter, to 0.060 inch for the 0.020 inch mill, the remaining 1.25 inch is 0.125 inch diameter. They should stay sharp for a long time being made of carbide.

In preparation for the 0.010 inch (250 μm) diameter tests, a group of in vivo resistance tests were repeated in subject's left inner wrist, approx. 1.5 inch back from the palm pad (last wrist wrinkle) using the SRC 715 LCR meter.

| | 120 Hz 0.25 V | 120 Hz 1.0 V | 1 KHz 0.25 V | 1 KHz 1.0 V |
|---|---|---|---|---|
| 2 Au strips ¾ × 2 on SC @ 2 inch separation | Out of range | 0. 0. R. | 383K ohms | 128K ohms |
| As above, In Normal (0.3 inch immerse) | 216 ohms | 200 ohms | 142 ohms | 138 ohms |
| Saline (0.8 inch immerse) | 94 ohms | 78 ohms | 60 ohms | 56 ohms |
| 2 #20 hypo needles to blood at 0.75 inch separate. | 12K ohms | 9K ohms | 5K ohms | 5K ohms |
| As above, In Normal Saline | 1.3K ohms | 1.3K ohms | 525 ohms | 490 ohms |
| 2 ECG electrodes over needle holes | 20K ohms | 13K ohms | 4K ohms | 4K ohms |
| 2 ECG electrodes on SC - no holes | Out of range | 0. 0. R. | 4K ohms | 4K ohms |

So, baseline is at 1 KHz, which clearly washes out resistance variations, and using the 1.0 volt potential, which shows large area gold strips (1.5 sq. in.) contact to the stratum corneum at 128 K ohms. The other bench mark is resistance in normal saline with Au being in the 140 ohm range (0.0187 sq. inch area) and stainless steel needles showing 500 ohm resistance (0.001 sq. inch area), which is probably roughly equivalent. So, the minimum resistance in vivo between two needles 0.75 inch apart in subject's blood is 5 K ohms, (a smaller area than in the saline by at least a factor of 50, since only the tips were in me). The 4 K ohms between two ECG electrodes was also seen in the above discussed tests, but it is expected that the stratum corneum removal reported on earlier did reduce the ECG resistance further, since putting the ECG over the holes did reduce the measured resistance for the 120 Hz tests, versus placing the ECG electrodes on unopened stratum corneum, where the resistance was very high at that frequency.

A 0.010 inch diameter (25 μm) endmill was used on three locations on subject's left hand, inner wrist. In this case, as before, the endmill was lifted back up from the bottom edge of the nose piece ring so that in pressing subject's wrist against the ring, the skin would be stretched and bulge up into the cavity formed by the ring until it touched the spinning endmill. Once the endmill had removed subject's stratum corneum, the resistance drop between the endmill and the ECG electrode would trigger the sensing circuit (set at 31 K ohms) and yank the mill away from subject's skin. The experiment was to run the mill motor at three different speeds as determined by the motor current to see if there was any difference in the look of the microconduit through subject's stratum corneum. Starting at 50 ma, the process worked well, and the microconduit is barely visible. Next, 40 ma was used, producing another small microconduit. Finally, at 30 ma, it was decided to disable to sense circuit and see what would happened. By this point, the approximate pressure with which subject's wrist needed to be pressed against the end ring to touch the mill was known, so subject's wrist was pushed a little harder. Interestingly, subject still couldn't feel a thing, but clearly the mill went deeper and there was even an ooze of blood seen at the lower edge of the microconduit. This suggests that perhaps one can get blood samples for glucose tests.

An ECG electrode was then put over the 30 ma microconduit and a second ECG put over the 40 ma and 50 ma sites together. Pressing the electrodes firmly against subject's skin, the resistance varied between 500-800 ohms (at 1 KHz and 1 Volt) The two electrodes were about half an inch apart, and when pressed on unpenetrated skin at the same spacing, they measured 4,500-5000 ohms. This indicated that stratum corneum removal reduces thru-skin electrical resistance to nearly the normal saline solution range as seen above The diameter of the 30 ma opening was also measured using a dial caliper and a calibration on the TV monitor and was found to be between 0.010 inch-0.011 inch (250-275 μm), indicating that the endmill was not fluttering. These openings are and remain invisible to the eye unlike the 0.020 inch diameter microconduits.

It is undetermined what the endmill drive motor speed is at those currents, but it is specified at 7,500 rpm at 75 ma and 1.3 volts. Thus the estimated revs would be 3000 rpm at 30 ma, 4000 rpm at 4 ma and 5000 rpm at 50 ma. There seemed to be no observable difference in the microconduit opening process.

The blood ooze when drilling somewhat deeper needs to be explored. Knowing that in subject's case the capillary bed is in the range of 100 μm-150 μm (from previous microscission experiments) this implies that the opening was perhaps 60 μm-100 μm deep. Assuming that, it was remarkable that subject didn't feel anything, so additional experiments around this depth range should be conducted. This could be done by reducing the trigger resistance from 3.1 K ohms to 25?, 15? K ohms. It is unknown at this point how much deeper that would allow the endmill to penetrate. Another approach would be to put a time delay in between the trigger resistance sensing and the drill motor pull-out. However, the next experiment would be about Lidocaine uptake through one of these milled stratum corneum microconduits.

Experiment 6

Drug Delivery—Lidocaine Uptake

The 50% Lidocaine solution (2.5 gms Lidocaine, 50 ml saline) used in the chemical uptake experiments for the microscission work was prepared. Running the endmill at 30 ma (about 0.5 volts) a deep microconduit was opened by disabling the rapid pullout. Here again, there was no sensation, but a drop of blood immediately welled up to the surface. The subject's wrist was wiped clean with de-ionized water, dried and a drop of Lidocaine put on the microconduit. Fresh Lidocaine was added to the puddle at 2 minutes and rinsed it off at 4 minutes with de-ionized water. Using the pin stick method, the microconduit was probed while observing it on the TV at the standard magnification. The skin was numb within a 200-250 micron (approx. 0.010 inch) radius. The microscission work showed a radius of 350 µM for a 2-3 minute anesthetic exposure. Thus, one can put chemical into the body through these microconduits and also likely remove analyte via the blood from the same microconduits.

A careful examination of the microconduit site after approx. 60 hours showed full healing. There was no sign of the microconduit, making the location of the site itself a time consuming process. This is quite different from the microscission experience, where complete healing took 14+ days. Perhaps this implies that there was not an open microconduit, as was clearly the case with the microscission process.

Tests at trigger resistances below 31 K ohms are needed to explore the endmilled microconduit characteristics.

Experiment 7

Trigger Resistance Below 31 K ohms

The trigger resistance was reduced from 30.1 K ohms to 20.3 K ohms. Again, running the endmill drive motor at 30 ma, the auto pullout was activated and subject's L.H. inner wrist pressed against the nosepiece. Everything worked, the mill pulled away, subject didn't feel a thing and there was a nice, small drop of blood by the time the microscope inspection took place. Use of the glucose tester wasn't attempted, but it did not appear that there was enough blood—the drop was about 250 µm in diameter.

Using a water soaked artist's brush, the endmill was washed off, the brush examined under the microscope and a disk of subject's stratum corneum discovered. An extrapolation of measurements of its width and thickness suggests that it is about 50 µm (0.002 inch) thick.

Data from L. A. Goldsmith's Biochemistry and Physiology of the Skin describes the stratum corneum as being composed of about 19 layers of fully keratinized metabolically inactive cells, each being approx. 0.55 µm thick, making the stratum corneum on the order of 10.4 µm (0.0004 inch) thick. (This is not true of the hand or foot pads, where there are about 39 layers of cells, with each cell being 30×0.55 µm (16 µm) thick, making that stratum corneum 400-600 µm (0.020 inch) thick.) Goldsmith reports the epidermis is 75 to 150 µm thick (0.003 inch to 0.006 inch.) So, this microconduit is approximately halfway into the epidermis (assuming the doughnut hole thickness estimate is about right.)

Forty Eight hours after the microconduit was made, it is visible at magnification, but cannot be seen with the unaided eye. It never exhibited the redness accompanying the microscised microconduits, even those that were 50-70 µm deep. Further, it seems more completely healed, making one wonder if the absence of any particulate in this milled microconduit enhances the healing rate. An interesting result, particularly the absence of sensation. One wonders whether the speed of the procedure, the whole thing takes less than a second, has something to do with no sensation.

Experiment 8

Electrically Non-Conducting Covering on Drill Tip

A new concept is being considered that could be used with the endmill (or drill) to permit setting the depth of penetration through the stratum corneum and into the epidermis and dermis and beyond. This concept isn't necessarily applicable to drilling nails, as the goal—as with drilling stratum corneum—is to reach high conductivity (low electrical resistance) between the cutting tool—body—EGG electrode a capability that has been demonstrated repeatedly.

The recent work with reducing the trigger resistance from about 30 K ohms to 20 K ohms demonstrated that one can move deeper into the body using resistance sensing alone. Nevertheless, this is a limited, relatively inaccurate technique, because it seems the minimum trigger resistance is about 5 K ohms or higher and the trigger resistance band is thus limited to 20/25 K ohms, likely with poor resolution.

However, the endmill can be placed to any depth with a resolution of perhaps 2.5-5 µm (0.0001-0.0002 inch) in the following manner. It is possible to coat the endmill from the cutting edges on back for any length with better dimensional resolution than above, using a material having high electrical resistance, that will not affect the cutting ability of the endmill. When such an endmill removes the stratum corneum this material will mask the lowered electrical resistance of the inside of the body, and will continue to do so to a depth equivalent to the length of the coating on the endmill. As soon as the endmill moves beyond that depth, the uncoated, electrically conductive portion of the endmill begins to enter the body. It makes contact with the low resistance tissues and fluids allowing the electronics to trigger pullout, or stop drill motor, or other electrically actuated actions.

Silicon Dioxide ($SiO_2$), Silicon Nitride ($Si_3N_4$) Aluminum Oxide ($Al_2O_3$) or a number of other hard, very thin, electrically insulating materials could be inexpensively applied with great dimensional accuracy along the endmill, from the cutting edge on back. These compounds may be as thin as a few molecular diameters (0.001 microns) up to 100+ microns (0.004 inches) or more, so that their presence on the cutting edges of the endmill would not be deleterious to the endmill's capability to cut living tissue. Also, the assumption is that the soft tissues encountered in the body would not wear off the insulating layer during the cutting process.

These materials, used extensively in Integrated Circuit (I.C.) fabrication, are well understood and characterized. Furthermore, they are inexpensive to apply, using D.C. or R.F. Vacuum Sputtering, Ion Beam Deposition, Plasma Deposition, Molecular Epitaxy, Chemical Vapor Deposition (CVD) Plasma Enhanced Chemical Vapor Deposition (PECVD), Anodization, Plasma Arc Coating, Electroplating and other well developed techniques. These processes are suitable to mass production and reliable.

Since the cutter penetration depth is set by a fixed coated length, different cutters would be needed for different depths. Cutters could be reused, easily interchanged on the motor that turns them and stripped, resharpened and recoated many times. This depth gauge should be independent of skin deflection, because the depth of tissue removal is determined by the coating on the cutter rather than the position of the entry point.

These very sharp endmills do not compress the skin much and cut quickly. With minimum tissue compression, the rapid material removal (drilling rate) and fast withdrawal will result in little or no sensation (pain). It is suspected that tissue compression may sensitize the nerves, preparing them for tissue damage detection. If there is no compression, rapid tissue removal, and cutter withdrawal (all in less than 0.5 seconds) perhaps even deep (0.1+ inch) microconduits can be generated with no pain.

In a similar concept, hypodermic needles might be sharpened concentrically, or even with toothed edges like hole saws and spun to cut the skin with less sensation (#33 needles have an O.D. of 0.008 inch. If they could be inserted with minimum sensation by the spin/cut process, they could carry insulating coatings in the same fashion as above to predetermine depth. Since they would be like cork borers, tissue might plug their bores, which could possibly be sucked out before putting in chemical, or withdrawing analyte. Then too, such needles could certainly be used to take off the stratum corneum, even go in a bit further using the lowered trigger resistance trick, which could be useful for putting in chemical.

Experiment 9

Blood Sampling

The FastTake glucose tester, made by Lifescan, was used in further experiments. Three experiments were run to see about getting enough blood to do a glucose test on. In all three cases the resistance-triggered pullout function was disabled. In the first test the nosepiece-to-endmill spacing was left as before and subject's left hand inner wrist pressed against the nosepiece. Subject felt nothing. Upon inspection, blood was visible. However, there wasn't enough to form a big enough drop to be capillaried into the test strip analysis chamber. Next the nosepiece was moved up, making the endmill protrude more deeply into the nosepiece. This way, when subject pressed skin bulge in, the endmill would make a deeper hole. Again, no sensation, some blood but not enough. Finally the nosepiece was removed and deeper drilling proceeded with visible inspection, the endmill went in perhaps 0.025 inch, then its flutes grabbed subject's epidermis and lifted it up the sides of the endmill. Subject just barely felt a tiny something. There was hardly any blood, but quite a bit of clear fluid.

Perhaps the 0.020 inch endmill should be tried rather than the 0.010 inch. The microconduit was deep enough and the lack of sensation was interesting. Further experimentation should be tried using a lower trigger resistance to see what that does. Using a 0.020 inch diameter endmill, 20 K ohm trigger resistance, and trying two different microconduit depths, another blood drop test was performed. One process was to bypass the resistance triggered pullout and press subject's skin against the spinning endmill. Subject just started to feel something—a slight prick sensation—and withdrew his wrist. Using a ruler consisting of a hypodermic needle, laser marked in 100 μm (0.004 inch) increments, it is clear that microconduit is about 120-150 μm (0.004 inch-0.006 inch) deep. A drop of blood came out which was transferred into the capillary chamber of the Lifescan FastTake test strip. It filled about half of the chamber (the top of which is transparent for observation) which was not enough to test subject's glucose level. That chamber requires 1.5 μL of blood to fill. The same company now makes an instrument with a 1.0 μL chamber. Other glucose monitors have test chambers that test as low as 0.3 μL blood volumes. There was more blood than 0.3 μL, but a tester that measures these smaller volumes will be required to prove these findings.

A blood glucose tester brand FreeStyle made by Therasense Co. located in Alameda, Calif. will test blood volumes as low as 0.3 μL rather than the 1.5 μL volume needed by the FastTake tester. A FreeStyle system was purchased and tests begun. There was difficulty getting blood out of subject's inner wrist near the hand. For some reason the endmill produced microconduit does not free up as much blood as the microscission process.

FreeStyle suggests use of the top of the arm, back toward the elbow for getting enough blood. Several tests were performed there, getting enough blood, but subject body hair made it difficult to place the test strip opening without smearing the blood around. An area was then shaved, the 0.020 inch diameter endmill was used without auto-out as described above, and a microconduit was made. The subject's arm was patted to bring blood to the surface, and squeezed around the microconduit, which produced a nice blood drop. It worked well with the FreeStyle with a reading 110 mg/dl, which is within normal range. Even the FastTake unit gave a reading of 87 mg/dl, which is low, but since the chamber was only half full, a low result was predicted by the instruction manual.

So, proof of concept has been completed on measuring blood glucose from a blood drop obtained through a microconduit made with the endmill. The slightest sensation was detected in this test, but nothing resembling the pain felt from a stab by the lancet supplied by the glucose tester manufacturers.

The 0.010 inch diameter endmill was revisited to see if a microconduit opened with that will supply enough blood for glucose testing using the 0.3 μL volume tester. The 0.020 inch tests showed that there was enough blood to fill the 0.3 μL test strip volume, and approximately 0.8 μL of the 1.5 μL test strip. That adds up to 1 μL, so if about half of that can be obtained out of a 0.010 inch diameter microconduit, the opening will be invisible, will heal faster and perhaps will generate less sensation during drilling.

Using a 0.010 inch diameter endmill, a microconduit was opened in the same locality on subject's upper forearm as described above. Readings were obtained using both the Freestyle and Fasttake glucose sensors. Freestyle (0.3 μL) read 87, while FastTake read 73 mg/dl. Both are within the physiologically normal range, with the F.T. still being lower. The same technique of patting the area and squeezing around the microconduit was used. The redness around the 0.010 inch diameter microconduit is much redder than seen in the microscope. The unaided eye view of the forearm site can only just perceive (if you know its there) the microconduit. Comparatively, it is less visible than subject's hair follicle sites.

Returning to the depth-setting concept described above, there are several possible variations on this theme to consider. In order to be practical in medical applications, the through-skin cutting tools must be 'one patient use' only. So, the previous discussion regarding tool wear is useful only for research interest, not for patient use. The design considerations must assume that a cutting tool would be used perhaps no more that about ten—twenty times (on the same patient) before being disposed of, and typically much less than that in a majority of cases.

Accordingly, the cutting tool could be an insulating material (glass, plastic, carbon, or other) the end of which was formed into a cutting surface by chemical or plasma etching or mechanical means. One embodiment would be to make the cutting surface by etching a multiplicity of closely spaced openings, leaving the interstices of triangular, sharp edged fibers. As described above, this could be coated, but with a thin, deposited, electrically conductive layer (rather than insulating) extending the full length of the insulating fiber or to within a predetermined distance back from its cutting-surfaced end (eliminating any coating on the cutting surface itself). In this case, the conductive coating would have to last long enough to withstand perhaps ten microconduit drillings. Such materials such as nickel, chromium, platinum, iridium, stainless steel, etc., have adequate hardness and inertness to be likely candidates as coatings. The coating would be so thin (millionths of an inch) that its cost would be minimum.

In the case of using hypodermic needle stock as discussed above, in addition to an electrically insulating coating on the predetermined length of the needle end, a cutting end made of insulating material could be attached to the needle. For instance, the fiber discussed above could be placed in the needle bore—with the needle acting as the 'drill chuck'. This would provide a 'quick change' method of replacing the disposable fibers that had conductive coatings to within pre determined distances behind the cutting tips. Another embodiment would be to have replaceable drilling ends of fiber, having larger diameters than the hypodermic needle. The needle could fit into a hole in such an end, making electrical contact to its depth-determining conductive coating (which would have to go around the sides and back of the drilling end). The microconduit diameter would be determined by the diameter of the 'drill' head placed on the end of the 'drill chuck' and its depth determined by the spacing between the conductive surface and the cutting surface.

In a similar manner, hypodermic needle stock may be designed to be telescoping. Using a 'drill chuck' hypodermic needle driven by the drill motor, various diameter needles could be used to produce microconduits of various diameters as well as depths. Adapters between small 'drill' needles and the large 'drill chuck' could be made of telescoping needles, for example where the drill needle could be larger or smaller (fit over the outside diameter or inside of the inside diameter). Also one could use manufactured adapters, all of which fit the 'drill chuck' but with each having a different sized hole on the opposite end (drill end) to accommodate the various 'drills'.

Another potentially useful implementation would be the use of a mount for the impedance sensing drill that allows movement in one or more directions allowing for greater placement flexibility. For example if the direction of drilling is assumed to be along the Z-axis the mount could allow for movement along the X-axis and Y axis. In certain embodiments the mount may also allow for movement along the z-axis as well. In many application it may be beneficial to have the movement along the various axis to be computer controlled. In certain applications the actual drilling may also be computer controlled.

Other applications of the impedance sensing drill could include cosmetic uses such as decorative marking or engraving of nails, or using microconduits to introduce pigments or dyes into the skin. When combined with the mount mentioned above, especially in computer-controlled applications, very precise designs may be created very quickly with little or no pain to the recipient.

While the invention has been described with respect to specific experiments and examples including presently preferred modes of carrying out the invention, those skilled in the art will appreciate that there are numerous variations and permutations of the above described systems and techniques that fall within the scope of the invention as set forth in the appended claims.

The invention claimed is:

1. An impedance sensing drill comprising:
    a drilling assembly including a motor and a cutter which is adapted to be moved into and out of a tissue being drilled for the formation of microconduits;
    a control module mechanically connected to the drilling assembly for controlling the depth of drilling by the drilling assembly; and
    a sensor, electrically connected to the drilling assembly and the control module, for detecting a change in an electrical impedance of the tissue being drilled;
    wherein, upon detection of a change in the electrical impedance, the sensor sends a signal to the control module of the drill to automatically reverse the forward motion of the cutter to withdraw the cutter from the tissue, and thereby control the depth of the drilling.

2. The impedance sensing drill of claim 1, wherein the electrical impedance being measured is electrical resistance.

3. A method of forming a microconduit in mammalian tissue, which comprises the steps of drilling into the tissue with an impedance sensing drill according to claim 1, monitoring an electrical impedance of the tissue, and stopping the drilling into the tissue and automatically reversing the forward motion of the cutter with the control module when a change in the electrical impedance is detected, thereby forming a microconduit in the tissue.

4. The method of claim 3, wherein the mammalian tissue is selected from the group consisting of tissue, stratum corneum, epidermis, dermis, cartilage, nails, and bone.

5. The method of claim 4, wherein the mammalian tissue is nail tissue.

6. A method of forming a microconduit in mammalian tissue, which comprises the steps of drilling into the tissue with a drilling assembly including a motor and a cutter, monitoring electrical impedance of the tissue with a sensor, and stopping the drilling into the tissue and automatically reversing the forward motion of the cutter with a control module when a change in the electrical impedance is detected by the sensor, thereby forming a microconduit in the tissue.

7. The method of claim 6, wherein the mammalian tissue is selected from the group consisting of tissue, stratum corneum, epidermis, dermis, cartilage, nails, and bone.

8. The method of claim 7, wherein the mammalian tissue is nail tissue.

9. The method of claim 6, wherein the electrical impedance being measured is electrical resistance.

10. An impedance sensing drill comprising:
    a drilling assembly including a cutter;
    a control module mechanically connected to the drilling assembly for controlling the depth of drilling by the cutter;
    a sensor, electrically connected to the drilling assembly and control module for detecting a change in an electrical impedance of mammalian tissue being drilled; and
    a mount allowing the cutter to move into or out of mammalian tissue being drilled;
    wherein upon detection of a change in the electrical impedance in the mammalian tissue, the sensor sends a signal to the control module which automatically withdraws the cutter from the tissue.

11. The impedance sensing drill of claim 10, wherein the impedance sensing drill is computer controlled.

12. The impedance sensing drill of claim 10, wherein the mammalian tissue is selected from the group consisting of tissue, stratum corneum, epidermis, dermis, cartilage, nails, and bone.

13. The method of claim 12, wherein the mammalian tissue is nail tissue.

14. The impedance sensing drill of claim 10, wherein the electrical impedance characteristic being measured is electrical resistance.

15. An impedance sensing drill comprising a drilling assembly including a housing adapted to be placed in contact with a tissue being drilled;

a motor and a cutter rotated by the motor which is mobile in translation in the housing and which is adapted to be moved into and out of the tissue being drilled for the formation of microconduits;

a control module mechanically connected to the drilling assembly for controlling the translation of the cutter in the housing and into and out of the tissue being drilled; and a sensor, electrically connected to the drilling assembly and to the control module for detecting a change in an electrical impedance between the cutter and the surface of the tissue being drilled when the cutter is translated in the tissue being drilled;

wherein the sensor, upon detection of a change in the electrical impedance corresponding to a transition between portions of the material being drilled, sends a signal to the control module to automatically reverse the direction of the cutter, thereby withdrawing the cutter from the tissue being drilled, and thereby controlling the depth of the drilling.

* * * * *